(12) United States Patent
Rodefeld

(10) Patent No.: US 11,596,783 B2
(45) Date of Patent: Mar. 7, 2023

(54) BLOOD PRESSURE POWERED AUXILIARY PUMP

(71) Applicant: Indiana University Research and Technology Corporation, Indianapolis, IN (US)

(72) Inventor: Mark D. Rodefeld, Carmel, IN (US)

(73) Assignee: Indiana University Research & Technology Corporation, Indianapolis, IN (US)

(*) Notice: Subject to any disclaimer, the term of this patent is extended or adjusted under 35 U.S.C. 154(b) by 0 days.

(21) Appl. No.: 16/975,455

(22) PCT Filed: Mar. 6, 2019

(86) PCT No.: PCT/US2019/020985
§ 371 (c)(1),
(2) Date: Aug. 25, 2020

(87) PCT Pub. No.: WO2019/173495
PCT Pub. Date: Sep. 12, 2019

(65) Prior Publication Data
US 2021/0015983 A1   Jan. 21, 2021

Related U.S. Application Data

(60) Provisional application No. 62/639,289, filed on Mar. 6, 2018.

(51) Int. Cl.
*A61M 60/405* (2021.01)
*A61M 60/148* (2021.01)
(Continued)

(52) U.S. Cl.
CPC ........ *A61M 60/405* (2021.01); *A61M 60/148* (2021.01); *A61M 60/205* (2021.01);
(Continued)

(58) Field of Classification Search
CPC .. A61M 60/205; A61M 60/148; A61M 60/82; A61M 2250/00; A61M 60/232;
(Continued)

(56) References Cited

U.S. PATENT DOCUMENTS 3,667,069 A * 6/1972 Blackshear ......... A61M 60/148
623/3.1
4,335,997 A   6/1982 Ewing et al.
(Continued)

FOREIGN PATENT DOCUMENTS

CN   101695991   4/2010
CN   103002929   3/2013
(Continued)

OTHER PUBLICATIONS

EP 19763751.5, European Search Report, 7 pgs dated Oct. 21, 2021.
(Continued)

*Primary Examiner* — Kenneth Bomberg
*Assistant Examiner* — Adam W Brown
(74) *Attorney, Agent, or Firm* — John V. Daniluck; Dentons Bingham Greenebaum LLP

(57) ABSTRACT

Methods and devices for a self-contained device including a hydraulic motor and a hydraulic pump. Preferably, the motor is incorporated either within the interior of the pump, on the exterior of the pump, or a combination of the two. The pump increases the kinetic energy of the fluid by centrifugal means, and in some embodiments is a viscous impeller pump. Applications include building flow systems, industrial processes, and biological circulatory systems.

49 Claims, 24 Drawing Sheets

(51) Int. Cl.
*A61M 60/205* (2021.01)
*A61M 60/82* (2021.01)
*A61M 60/824* (2021.01)
*A61M 60/35* (2021.01)
*A61M 60/882* (2021.01)
*A61M 60/806* (2021.01)
*A61M 60/232* (2021.01)

(52) U.S. Cl.
CPC .......... *A61M 60/232* (2021.01); *A61M 60/35* (2021.01); *A61M 60/806* (2021.01); *A61M 60/82* (2021.01); *A61M 60/824* (2021.01); *A61M 60/882* (2021.01); *A61M 2250/00* (2013.01)

(58) Field of Classification Search
CPC .. A61M 60/35; A61M 60/806; A61M 60/861; A61M 1/00; A61M 60/882; A61M 60/405; F04B 17/00; F04D 13/04; F04D 29/22; F04D 7/02
See application file for complete search history.

(56) References Cited

U.S. PATENT DOCUMENTS

| | | | |
|---|---|---|---|
| 4,610,235 A | 9/1986 | Grunig | |
| 5,102,296 A | 4/1992 | Kimberlin | |
| 5,145,333 A * | 9/1992 | Smith | F04D 29/108 417/405 |
| 5,471,965 A | 12/1995 | Kapich | |
| 5,904,045 A | 5/1999 | Kapich | |
| 5,924,286 A | 7/1999 | Kapich | |
| 6,152,704 A * | 11/2000 | Aboul-Hosn | F04D 13/027 417/360 |
| 6,450,156 B1 | 9/2002 | Araujo | |
| 6,827,682 B2 * | 12/2004 | Bugge | A61M 27/002 600/16 |
| 7,044,718 B1 * | 5/2006 | Platts | F02C 3/045 415/206 |
| 7,210,908 B2 | 5/2007 | Keck | |
| 7,478,629 B2 | 1/2009 | delValle Bravo et al. | |
| 7,530,553 B2 | 5/2009 | Kapich | |
| 8,449,443 B2 * | 5/2013 | Rodefeld | A61F 2/06 600/16 |
| 8,453,999 B2 | 6/2013 | Kapich | |
| 8,684,904 B2 | 4/2014 | Campbell et al. | |
| 8,985,967 B2 * | 3/2015 | Gudivada | F04D 13/043 417/408 |
| 9,084,859 B2 | 7/2015 | Connor | |
| 9,314,558 B2 | 4/2016 | Er | |
| 9,327,067 B2 | 5/2016 | Zeng et al. | |
| 9,339,597 B2 | 5/2016 | Khanal et al. | |
| 9,364,592 B2 | 6/2016 | McBride et al. | |
| 9,364,593 B2 | 6/2016 | McBride et al. | |
| 9,533,084 B2 | 1/2017 | Siess et al. | |
| 9,597,206 B2 | 3/2017 | Seddon et al. | |
| 9,675,740 B2 | 6/2017 | Zeng et al. | |
| 9,717,833 B2 | 8/2017 | McBride et al. | |
| 9,764,113 B2 | 9/2017 | Tuval et al. | |
| 9,827,357 B2 * | 11/2017 | Rodefeld | A61M 60/205 |
| 2002/0103413 A1 | 8/2002 | Bugge et al. | |
| 2006/0254274 A1 | 11/2006 | Kapich | |
| 2006/0273194 A1 | 12/2006 | Kapich | |
| 2008/0183286 A1 | 7/2008 | Vaska | |
| 2009/0318748 A1 * | 12/2009 | Merce Vives | F04D 29/4273 600/17 |
| 2010/0280305 A1 | 11/2010 | Hidaka et al. | |
| 2012/0180480 A1 | 7/2012 | Kapich | |
| 2014/0051908 A1 | 2/2014 | Khanal et al. | |
| 2014/0336446 A1 | 11/2014 | Rodefeld | |
| 2014/0341709 A1 | 11/2014 | Yamodo | |
| 2015/0051438 A1 | 2/2015 | Taskin | |
| 2016/0172955 A1 | 6/2016 | Sirous | |
| 2016/0184500 A1 | 6/2016 | Zeng | |
| 2017/0043075 A1 | 2/2017 | Corbett et al. | |
| 2017/0100528 A1 | 4/2017 | Wampler et al. | |
| 2017/0239406 A1 | 8/2017 | Zeng et al. | |

FOREIGN PATENT DOCUMENTS

| | | |
|---|---|---|
| CN | 103480053 | 1/2014 |
| CN | 104185481 | 12/2014 |
| CN | 104984424 | 10/2015 |
| DE | 102015204399 | 9/2016 |
| EP | 0475500 | 3/1992 |
| EP | 1767778 | 3/2007 |
| EP | 3173109 | 5/2017 |
| JP | 4310552 | 6/2010 |
| WO | 1999040303 | 8/1999 |
| WO | 1999056017 | 11/1999 |
| WO | 2003010433 | 2/2003 |
| WO | 2006137696 | 12/2006 |
| WO | 2007104973 | 9/2007 |
| WO | 2012107617 | 8/2012 |
| WO | 2013082621 | 6/2013 |
| WO | 2013119752 | 8/2013 |
| WO | 2013148697 | 10/2013 |
| WO | 2014164292 | 10/2014 |
| WO | 2014191254 | 12/2014 |
| WO | 2015177793 | 11/2015 |
| WO | 2016115595 | 7/2016 |

OTHER PUBLICATIONS

PCT/US2019/020985, International Search Report and Written Opinion, 12 pgs dated May 24, 2019.

* cited by examiner

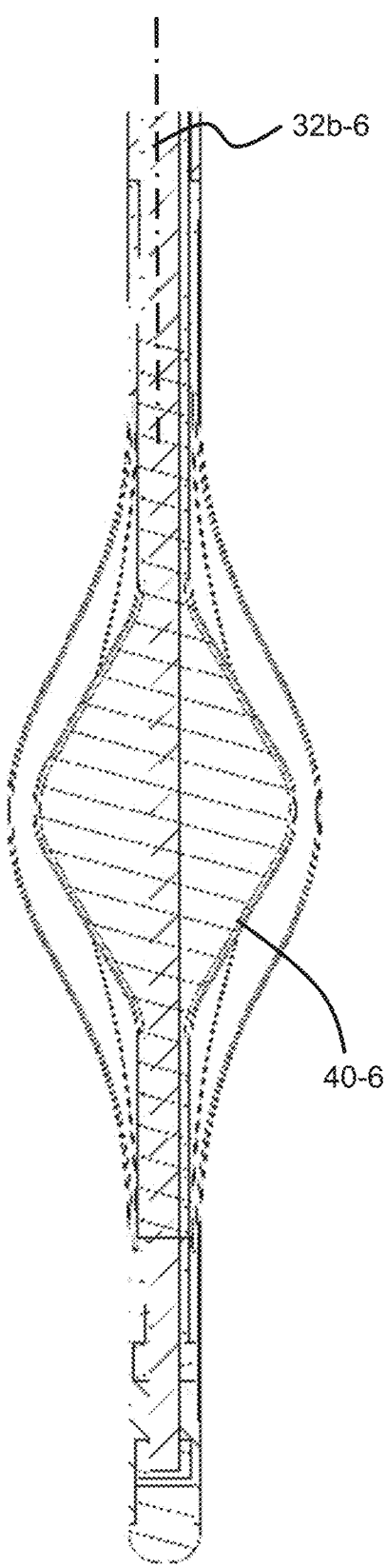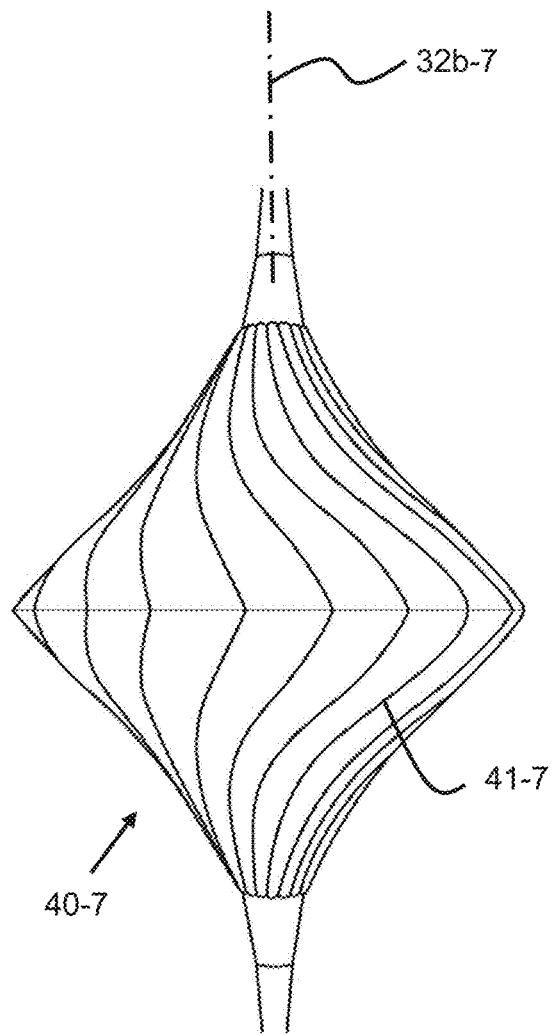
FIG. 4H
FIG. 4G

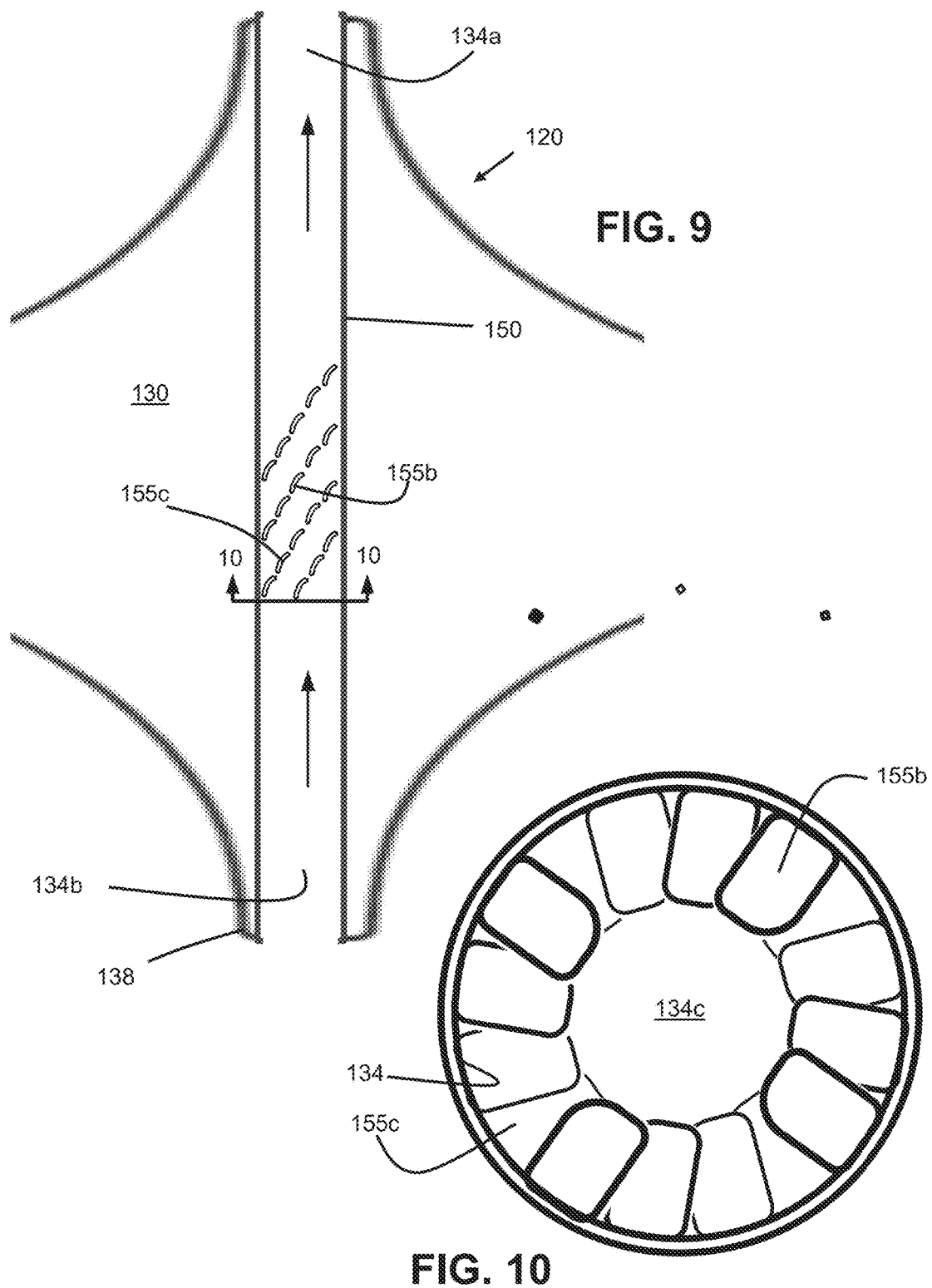

BLOOD PRESSURE POWERED AUXILIARY PUMP

CROSS REFERENCE TO RELATED APPLICATION

This application claims the benefit of priority to U.S. Provisional Patent Application Ser. No. 62/639,289, filed Mar. 6, 2018, titled BLOOD PRESSURE POWERED AUXILIARY PUMP, incorporated herein by reference.

FIELD OF THE INVENTION

Various embodiments of the invention relate generally to the field of pumps including blood pumps, including non-positive displacement pumps of rotary design, and including those suitable for permanent implantation in animals for use in circulatory support as well as those suitable for industrial and laboratory use.

BACKGROUND OF THE INVENTION

Some children are born missing half their heart. Known as single ventricle heart disease, it is the leading cause of death in children less than one year of age from any structural birth defect. One common anatomic variant is Hypoplastic Left Heart Syndrome. Until recently this condition was not compatible with survival. Beginning in the 1970's, developments in the surgical treatment of single ventricle heart disease have resulted in a means of not only survival, but also reasonable quality of life for survivors at least into early adulthood. Current therapy includes a series of 3 staged open heart procedures. While these procedures offer hope for survival, they remain problematic and notorious for instability and mortality. The staged surgical reconstruction of the circulatory system culminates in a univentricular Fontan circulation, eponymous with Dr. Francis Fontan who first described the repair in 1971.

In a univentricular Fontan circulation, the single ventricle (pumping chamber) is committed to provide blood flow to the body. Opposed to a normal 2-ventricle circulation, however, blood flow through the lungs is not supported by a ventricular power source; it should rather flow through the lungs passively. Therefore, the motive force for blood flow through the lungs rests upon systemic venous pressure alone. As a consequence, systemic venous pressure is markedly elevated and systemic venous return is significantly altered. This sets up a new set of hemodynamic problems, described by de Leval as the Fontan paradox, in which elevated systemic venous pressure coexists with relative pulmonary arterial hypotension. Preload to the single ventricle is reduced, as well as cardiac output. Patients with a univentricular Fontan circulation are therefore at high risk for late Fontan failure and attrition.

The late consequences of this circulatory arrangement are now an emerging public health concern. Thousands of patients who survive Fontan palliation are expected to present with Fontan failure. The insidious complications of chronically elevated systemic venous pressure include hepatic and gut dysfunction, protein losing enteropathy, leg swelling, and collection of fluid in the abdominal and chest cavities. The insidious complications of chronically reduced preload include late ventricular diastolic dysfunction, and poor systemic tissue perfusion. Targeted medical therapeutic options for Fontan failure do not exist. For example, while diuretic therapy may improve symptoms of increased tissue/organ edema, it does so at the expense of circulating blood volume which is helpful to Fontan circulatory homeostasis. Similarly, although the use of inotropic support may improve myocardial contractility, this is of marginal impact in an insufficiently filled ventricle. Heart transplantation is a poor end-stage option: Transplantation carries morbidity of its own, and the donor pool is limited. Few patients will ultimately be candidates or receive a donor organ for transplantation.

The development of a permanent right-sided circulatory support device directly addresses the Fontan paradox and will improve late quality of life and outcomes for those born with single functional ventricle. One aspect of some embodiments has been to include power sources to support the univentricular Fontan circulation. The placement of a power source at the level of the total cavopulmonary connection effectively empowers the univentricular Fontan circulation by placing a right ventricle equivalent back into a circulation that lacks one. By simultaneously reducing systemic venous pressure and improving ventricular preload, normal 2-ventricle physiology can be effectively restored.

Prior applications of existing blood pump technology have been contemplated to address the problem of powering the Fontan circulation. These have consisted primarily of applying intravascular unidirectional axial flow pumps to augment Fontan flow. The concept of cavopulmonary assist was introduced in 2003 with the simultaneous use of 2 unidirectional axial flow pumps (Rodefeld et al, Ann Thoracic Surg). This has limitations, however, as one-way flow devices will cause undesirable back-pressure elevation in the opposing vena caval territory. Other groups have followed with modifications of axial flow pump designs intended to operate in the low-pressure systemic venous circulation. This has also included a modification of the preferred TCPC Fontan venous pathway to a 3-way pathway so that the pathway better accommodates a unidirectional pump in a common unidirectional outflow limb. Although in theory this is possible, the 3-way vascular configuration is not the preferred hemodynamic pathway in an unsupported Fontan circulation.

What follows are various improvements in the field of non-positive displacement, motor-driven circulatory pumps that overcome some of the disadvantages of existing systems.

SUMMARY OF THE INVENTION

One embodiment of the present invention pertains to a pumping assembly that operates in a fully autonomous mode when it is supplied fluid from a higher pressure of a source of fluid, and the fluid flows to a lower pressure of the source of fluid. The pump includes a centrifugal pumping element powered by a hydraulic motor. The pumping assembly begins and maintains operation by fluid communication with the source, and preferably does not need any external intervention, or any external or internal electrical or mechanical power. It is understood that the centrifugal pumping element and the motor are preferable integral, but can also be separate.

In some embodiments, the higher pressure fluid is provided simultaneously (such as by a T-shape or Y-shape junction) to both the inlet of the motor and to the inlet of a restriction. The restriction can represent a subsystem that makes use of the pumped fluid, such as by exchanging heat with the system or supplying chemicals carried in the fluid to the system, as non-limiting examples.

After the fluid exits the restriction or subsystem (which is understood to include a variety of different fluid passageways and devices arranged in any manner), the fluid that flowed through the subsystem is provided to the inlet of a centrifugal pump. This pump is mechanically driven by the hydraulic motor. In some embodiments, the higher pressure fluid exiting the pump can be provided to yet another restriction (representing yet another system similar to that previously described), or simply returned to the source of fluid.

In other embodiments, the fluid exiting the hydraulic motor is returned to the source of fluid, which is at the lowest pressure in the overall fluid flowpath. In yet other embodiments, the fluid exiting the pump is added to the fluid exiting the hydraulic pump, and thereafter the combined flows are provided to either the restriction representing the second system, or to the inlet of the source of fluid. In the former embodiment, it can be seen that the pressure drop across the hydraulic motor is greater than in the latter system.

In some embodiments, the aforementioned autonomous pump and motor need only a source of high pressure fluid, and a sink for low pressure fluid. The pump and motor will thereafter operate with an energy draw based on the flow and pressure characteristics of the source of fluid, based on the flow characteristics of the restrictions, and based on the geometry and features of the pump and the motor. In those embodiments not including any variable geometry, the pump and motor will come to an operating point based on these aforementioned characteristics. The rotational speed of the pump and motor, as well as the pressure and flow characteristics of the pump, are influenced upon the aforementioned characteristics. For example, increasing the pressure of the source of fluid will in some embodiments tend to make the hydraulic motor run faster. As yet another example, a decrease in the fluid resistance of the restriction (i.e., corresponding to an increase in flow number and flow rate), will lead toward lower motor speed (because of the reduced flow to the motor, and further because of the increased quantity of fluid being pumped).

In some embodiments of the present invention, the combination of centrifugal pump and hydraulic motor is useful in any type of flow system, especially those systems in which it is helpful to boost the pressure at the exit of a first restriction, and prior to providing that flow to the inlet of a second restriction. In still other embodiments, the various pumping assemblies described and shown herein are helpful in managing the flow characteristics of a recycling, closed loop fluid system.

As will be shown and described in yet other embodiments, this boost in an intermediate pressure of the overall flow system is provided by using some of the fluid power that would otherwise be presented to the first restriction, but is instead used to drive the hydraulic motor. Preferably, the overall flow system is a closed flow system, in which flow from a source of highest pressure is provided to the various components (motor, pump, restrictions), and then fed back to the source in a close loop manner.

The motors and pumps described herein are helpful in boosting the pressure and flow to a second restriction, with this flow to the second restriction depending not only on the characteristics of the first restriction (as in most flow systems), but also depending upon the characteristics of the motor and the pump. Examples of such flow systems include residential and commercial buildings, industrial processes, and the circulatory system of biological units. Although what will be shown and described herein pertains in many embodiments to a circulatory system, it is understood that the various concepts and devices are more general than that.

Although what is shown and described in some embodiments is an overall fluid flow system having a source, a hydraulic motor, a centrifugal pump, and one or more fluid subsystems that restrict flow, in yet other embodiments of the present invention there is no requirement for either restrictions or subsystems of fluid systems within the overall fluid flow system. Further, it is understood that in those applications that do include fluid subsystems that provide flow restrictions, that those fluid subsystems can be a single subsystem placed after the motor or after the pump, or multiple subsystems arranged in series or parallel.

It is a further aspect of some embodiments to provide a means for pumping blood or other liquids using a rotary impeller located in the midst to the bloodstream or the fluid passageway.

It is a further aspect of some embodiments to provide an implantable motor to drive the implanted rotary impeller, with these implanted devices not requiring electrical power.

It is a still further aspect of some embodiments to provide an implantable motor that receives hydraulic power from the circulatory system and provides that power to driving another implanted component, such as a pump or an electric generator.

A still further of some embodiments is to provide an implantable hydraulic motor that converts power from the circulating flow of blood without use of a positive displacement arrangement.

Yet another aspect of some embodiments is to provide an implantable hydraulic motor that drives an electric generator, the power from the electric generator preferably being used to power other implanted electronic devices.

It is still a further aspect of some embodiments to provide a means for pumping blood or other liquids that does not use a positive displacement pumping arrangement.

If is a further aspect of some embodiments to provide a compact rotary blood pump which has no potential to obstruct the blood flow pathway or the fluid passageway.

It is a further aspect of some embodiments to provide a rotary pump which uses blood or the pumped fluid as a bearing material.

It is a further aspect of some embodiments to provide a rotary pump which uses passive magnetic bearings to suspend the rotating element in a radial and axial fashion;

It is a further aspect of some embodiments to provide hydrodynamic and thrust bearings in an arrangement in the event of touchdown due to device external shock or imbalanced operation.

It is a further aspect of some embodiments to provide a permanent Fontan pump which will afford the opportunity to address right/left lung blood flow disparity.

It is a further aspect of some embodiments to provide a permanent Fontan blood pump which will afford the opportunity to address vessel stenoses at the time of device implantation.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 4G is a side elevational partially cutaway view of an expandable viscous impelling pump according to yet another embodiment of the present invention.

FIG. 4H is a side elevational CAD-generated schematic representation of a viscous impelling pump according to yet another embodiment of the present invention.

FIG. 9 is a cutaway portion of a schematic representation of a portion of a motor-driven pumping apparatus according to another embodiment of the present invention.

FIG. 10 is a view of the apparatus of FIG. 9 as seen looking from line 10-10 of FIG. 9.

ELEMENT NOMENCLATURE

Figure 1A:
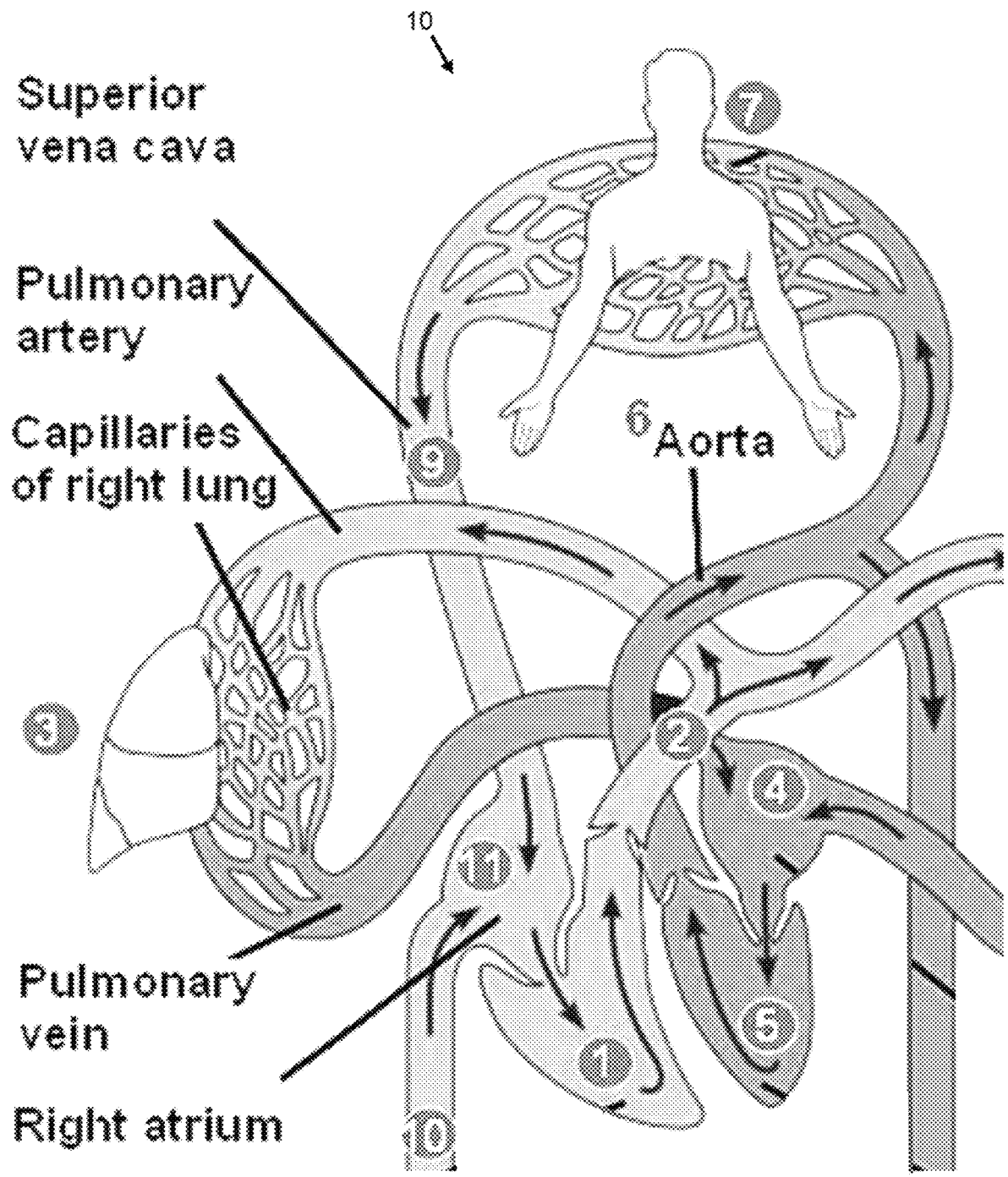
FIG. 1A is a schematic representation of a portion of the circulatory system of a human.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | circulatory system |
| 12 | Fontan junction |
| a | source/inlet |
| b | receiver/outlet |
| 14 | supply from left ventricle |
| 16 | supply to left atrium |
| 17 | to lungs |
| 18 | branching artery |
| 20 | implantable pumping device; means for centrifugally pumping |
| 22 | housing |
| 23 | Fluid or blood flowpath |
| a | inlet |
| b | outlet |
| 24 | supports |
| a | inlet |
| b | outlet |
| c | inlet shroud |
| d | stationary vanes |
| e | internal extension |
| f | nozzle |
| 25 | struts |
| a | strut extension |
| 26 | fluid connection |
| a | first (inlet) |
| b | second (outlet) |

| | |
|---|---|
| 27 | supply shunt |
| 28 | return shunt |
| 29 | bearing stationary |
| 30 | body |
| 32 | shape |
| a | plane of symmetry |
| b | rotational axis |
| 34 | passageway, motive flow, enclosed |
| a | inlet |
| b | exit |
| c | unobstructed portion |
| 36 | internal passageway, secondary flow |
| a | apex flow |
| b | wake flow |
| c | boundary control flow |
| d | inlets |
| 38 | supported end |
| 39 | bearing rotating |
| 40 | impeller |
| 41 | impelling blade |
| 42 | outer surface |
| a | inlet |
| b | outlet |
| 43 | viscously impelled external flow |
| a | streamline |
| 44 | apex |
| a | apertures |
| 46 | inlets |
| 48 | outlets |
| 50 | hydraulic motor; means for hydraulically powering |
| 52 | closed flowpath |
| 54 | opened flowpath |
| a | mixing region |
| 55 | motive conversion features, elements |
| a | long blades |
| b | short blades |
| c | buckets |
| d | spiral blade |
| e | multiple spiral blades |
| 56 | inlet |
| 58 | outlet |

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that some features 1020.1 and 20.1 may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), and triple prime ('") suffixed element numbers. Therefore, it is not necessary to describe the features of 20.1, 20.1',20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Various references may be made to one or more methods of manufacturing. It is understood that these are by way of example only, and various embodiments of the invention can be fabricated in a wide variety of ways, such as by casting, sintering, sputtering, welding, electrodischarge machining, milling, as examples. Further, various other embodiment may be fabricated by any of the various additive manufacturing methods, some of which are referred to 3-D printing.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

Various embodiments of the present invention pertain to apparatus and methods for providing a pressure increase within a flow system by using some of the energy provided by a fluid source to drive a motor that in turn drives a pressure-increasing pump within an overall flow system.

Although various embodiments will be described with regards to circulatory systems of biological units, it is understood that the various designs herein are applicable not only as implanted devices in a living organism, but further as pumping devices in industrial and laboratory settings.

Various embodiments include a centrifugal pump or impeller that is powered by a hydraulic motor. In some applications, the impeller imparts an increase in the energy of the fluid by centrifugal action of the impeller, such as by rotating blades, a rotating smooth surface, or combinations of both.

The impeller is preferably incorporated onto a portion of a rotating body, with yet another, different portion of that same body being adapted and configured to operate as a hydraulic motor. The hydraulic motor is provided with fluid from a pressure that is higher than the pressure received at the inlet of the impeller or provided at the outlet of the impeller, and is further of the same type of fluid to which the impeller is imparting work. By powering the hydraulic motor with a higher pressure source of the same fluid, it is not necessary to isolate the fluid providing motive power from the fluid whose energy is being increased. Although it is desirable in some embodiments to keep the motive fluid separate from the impelled fluid, since the two fluids are of the same chemistry, the mixing of the two fluids does not present a problem to the biological unit or the industrial/laboratory flow system. However, yet other embodiments of the present invention contemplate the motive flow fluid being different than the impelled fluid, provided that the introduction of the motive fluid into the impelled fluid does not present a problem to the biological unit or to the flow system.

In a preferred embodiment, the motive power for the fluid is provided from a relatively high pressure source in the circulatory system, such as the output of the left ventricle. Blood at about the same pressure as blood at the output of the left ventricle is provided by way of an implanted shunt to the inlet of the hydraulic motor. This highest pressure blood provides motive power to the impeller. As this supply of blood exits the hydraulic motor, it is then provided back to the circulatory system in either a "closed" system (in which the motive flow blood flows through a second implanted shunt to a source of lower pressure, such as the inlet of the left atrium) or by way of an "opened" system in which the higher pressure blood providing the mode of power then mixes in any of a variety of ways with the blood flowing over the impeller.

In some embodiments having a closed flow system, the hydraulic motor is provided within an internal flow passage within the rotating body. As one example, the higher pressure blood can be received at one end of the rotating body, flow within a central passageway having one or more motive conversion features adapted and configured for converting energy from a flowing fluid into rotational energy, and then exit the rotating body. The higher pressure blood is provided through a shunt to a static strut of an inlet support structure.

After performing work by the hydraulic motor, the lower pressure blood would then exit through an outlet support and a corresponding static strut, and into the implanted shunt. It is understood that various types of motive conversion features can be used within the internal passageway, and in some cases these conversion features are modifications of the Pelton, Francis, or Kaplan hydraulic motive designs. Preferably, the internal passageway has a central portion that is free and clear of the motive conversion devices, so as to provide relatively low pressure losses in the event that the rotor stops turning.

In the open type of hydraulic motor, the inlet regions of the impeller incorporate one or more motive conversion features to impart rotational energy to the rotor. These features are located on the external surface of the pump, and therefore provide some degree of interruption of the flow which the impeller portion of the body is imparting work into. Preferably, these inlet sections are adapted and configured for improved hydraulic motor operation, such as in how the motive conversion features are configured and spaced out, and further with regards to accompanying static features such as close-fitting shrouds to minimize flow over the top of the conversion features (and thus forcing the preferred flow against the lateral surfaces of the conversion features), inlet nozzles to accelerate the velocity of the blood, inlet vanes to impart swirl, and other features. Still further, in various open configurations the body of the rotor is further adapted and configured to improve the impeller operation by means of boundary control or boundary assist, wake control, or wake-filling, and the like.

Still further open flow hydraulic motors provide flow to an internal passageway of the rotating body, similar to that of the closed designs. However, the flow then exits the internal passageway and flows into the blood surrounding the impelling surface.

In various embodiments shown herein, the impellers can be of any type, and examples are shown and described herein, and further in either of two PCT applications referenced herein. It is understood that any of these impellers, or others, can be integrated with the hydraulic motors described herein.

The bioengineering considerations to accomplish cavopulmonary assist are unique in a univentricular Fontan circulation. A chronic Fontan pump should: 1) deliver low pressure, high volume flow similar to normal right ventricular hemodynamics; 2) augment flow in 4 directions with axially opposed inflow and orthogonally related bidirectional outflow; 3) avoid thrombogenicity, preferably with a bearingless and sealless design; 4) have an expected durability of decades; 5) utilize a power source that is realistic for such long-term use; 6) should not obstruct flow in the Fontan venous pathway—whether the pump is functional or not.

A chronic rotary blood pump according to one embodiment of the present invention designed to support the Fontan circulation is surgically implanted into the total cavopulmonary connection (TCPC). This is the anatomic junction created between the superior and inferior vena cavae and the right and left pulmonary arteries during Fontan surgery. This anatomic configuration is in the shape of a '+' and is the preferred construction for passive venopulmonary blood flow in Fontan patients. The surgical implantation of a permanent cavopulmonary assist device in this location is technically similar to a Fontan conversion operation, and therefore reasonable to perform. It includes cardiopulmonary bypass, but not cardioplegic arrest. Once implanted, the pump provides 2-5 mmHg pressure augmentation to Fontan venous flow. Accordingly, this decreases upstream systemic venous pressure by 2-5 mmHg, and increases pulmonary arterial pressure by 2-5 mmHg, translating to increased transpulmonary blood flow, increased preload, and ultimately increased cardiac output. This low pressure pumping action provides a transformative improvement in circulatory status by restoring more stable 2-ventricle physiology.

The current disclosure is related to a means to self-power the pump, rather than use an external or internal power source. The viscous pump can be powered by a turbine or other hydraulic motor using systemic arterial pressure which is a higher pressure source than exists in the right-sided circulation. Using the pressure energy reserve in the systemic arterial circulation, the pressure differential can be used to hydraulically power a pump to augment flow in the low-pressure right-sided circulation. This would be of significant value because it would simplify the device, make it more user-friendly, and eliminate the need for continuous external power input.

Various embodiments preferably include one or more of the following aspects: 1) simplified device; 2) reduced failure risk and improved long-term durability; 3) reduced/minimal/no maintenance (place it and forget it), 4) activity responsiveness (exercise will increase systemic blood pressure, which will in turn increase right-sided circulatory support); 5) pumping can be phasic (pulsatile) and therefore more physiologic because drive will come from a pulsatile source; 6) eliminates the need for transcutaneous drivelines or complex wireless charging.

Various embodiments of the methods and devices shown herein pertain to the use of various types of hydraulic motors that power a non-positive displacement pumping element by means of energy taken from the circulatory system. In some embodiments, the hydraulic motor includes a rotating element that provides rotating mechanical energy by means of impulse and inertia from the flowing blood, although other embodiments of the present invention further contemplate obtaining the mechanical energy by reaction (or pressure) type devices. This can be done using high-pressure blood flow from the systemic circulation to rotate a turbine, which will in turn rotate a compressor (i.e. the viscous pump) to provide augmentation of right-sided cavopulmonary blood flow. Still further embodiments contemplate extending the methods and devices shown herein to circulatory support applications beyond single ventricle circulatory support.

Existing blood pumps are severely limited by the need for a continuous, external power source to ensure continuous operation of the device. This includes percutaneous drivelines which penetrate the skin and are a source for infection and driveline failure. This also imposes a heavy societal burden on the patient (unable to shower, swim, etc).

A self-powered viscous pump can theoretically be placed and "forgotten". It will self-sustain, and no maintenance is required (other than oral anticoagulation). It would eliminate drivelines and infection risk. It would enhance lifestyle for patients allowing them untethered benefit of the device, with no restriction whatsoever.

The invention proposes the use of systemic blood pressure and a "shunt" to provide a high-pressure source of blood flow to energize the viscous pump. The high-pressure inflow would actuate a turbine, which would in turn actuate a compressor (i.e. the viscous pump) to augment the lower pressure right-sided circulation. In some embodiments, a second shunt is used to provide flow from the hydraulic motor to a low-pressure source of blood flow. As the pump rotor spins, a viscous pumping action occurs along the outer surface, inducing flow from the inlets toward the outlets. This flow across the outer surface of the pump has a reduced static pressure proximate to the flow exit of the pump, although this flow exiting the pump has increased total pressure.

In the text and drawings of this document reference will be made to the use of a pump in the circulatory system of an animal. It is recognized still further that the apparatus and methods described herein further pertain to the pumping of a fluid in any similar arrangement of fluid passageways.

Various embodiments of the present invention pertain to a pump adapted and configured to provide a pressure assist to the cavopulmonary system of an animal. In some embodiments, the pump is packaged within a housing that is adapted and configured to be placed within the circulatory system of the animal on a permanent basis.

In some embodiments, the pump is of the non-positive displacement variety, and provides an increase in energy to the pump fluid by centrifugal action. Preferably, the centrifugal assist is applied to the working fluid by a viscous operation on the surface of a rotating element, although other embodiments contemplate that the centrifugal assist is provided by any of a variety of surface motive flow features that extend outwardly from the surface. In some embodiments, the rotating element is axisymmetrical, whereas in other embodiments the rotor is both axisymmetrical, and further symmetrical about a plane. Various embodiments of the present invention also pertain to devices and methods for centrifugal blood pumps 40, such as those described in international application numbers PCT/US09/59733 and PCT/US2012/067648, both incorporated herein for material describing the pumping of blood by various rotary impellers.

Some embodiments include a thin-walled rotor that rotates about a centerline. The rotor has an outer surface that is adapted and configured to centrifugally pump blood from outlets, this outlet flow inducing axially directed inlet flow. Preferably, the outer surface has an outer diameter that monotonically increases from either end of the rotor (these ends preferably being supported by struts) toward the middle of the rotor. In some embodiments, the rotor is axisymmetric about the rotational axis, and in still further embodiments, the rotor is further symmetric about a central plane that is generally perpendicular to axis. With this combination of axisymmetric and planar symmetry the rotor encounters no or only negligible net thrust loads along the axis or rotation.

The rotational axis of the pump preferably passes through a pair of opposing inlets. The shape of the rotor is adapted and configured to viscously induce fluid flow from the inlets and to centrifugally provide this same flow at a higher total pressure to at least one outlet. At least a portion of the cross-sectional area of the outlet is preferably intersected by the plane of symmetry.

Some embodiments include a rotor that is suspended about an internal stator by magnetic bearings or hydrodynamic bearings, or a combination of the two. In those embodiments having both axial and planar symmetry, there is little or no net thrust of the rotor relative to the stator, and the negligible net thrust can be accommodated by the hydrodynamic bearings. In some embodiments, the magnetic bearings are adapted and configured to provide both radial support and further a magnetic force that is resistive to any net thrust. These magnetic thrust bearings can include a second pair of magnetic bearings, in additional to a first pair of magnetic bearings that provide radial support of the rotor. In those embodiments in which the stator has a shape for viscously and centrifugally imparting energy to the fluid (such as a VIP pump), the first pair of magnetic bearings providing radial support may be located proximate to the opposing ends of the rotor, where the outer shape of the rotor is a relatively more parallel to the rotational axis. The second paramagnetic bearings providing thrust support may be located proximate to the center of such a rotor, where the outer shape of the rotor is relatively more parallel to a central plane of symmetry.

In some embodiments the rotating pumping element has the general shape adapted and configured for providing viscous and central focal action to the fluid, and further with both axial and planar symmetry. In some of these embodiments, the rotor comprises a thin-walled shell of a suitable biocompatible material. This rotor can be formed by any means, including, such as by die forming, forging, sheet metal stamping, 3D printing, injection molding, or any other means. In still further embodiments, the rotor may be of a two-part construction, and having a joining split line located along the central plane or along the rotational axis.

Pumps according to some embodiments of the present invention include stators having an external shape that is substantially the same as the internal shape of the rotor. In such embodiments, the close gap between the rotating and static members can be provided with a cushioning fluid, such as the fluid being pumped by the rotor. In those embodiments in which the rotor is a thin-walled shell, the outer surface of the stator can have substantially the same shape as the external shape of the rotor, and in those embodiments in which the rotor has VIP pumping characteristics, likewise the bearing flowpath between rotor and stator can have VIP pumping characteristics. For those pumps adapted and configured to pump blood in circulatory system of an animal, the size and configuration of the separating gap is adapted and configured to discourage clotting of the blood within the gap.

One embodiment of the invention disclosed herein solves these problems. The pump (40) disclosed is designed to permanently augment Fontan venous flow. It is modeled morphologically after the temporary percutaneous expandable von Karman viscous impeller pumps which are further described in International patent application Serial No. PCT/US09/59733, filed Oct. 6, 2009, and titled ACTIVE OR PASSIVE ASSISTANCE IN THE CIRCULATORY SYSTEM, and also in International patent application Serial No. PCT/US2012/067648 and titled CAVOPULMONARY VISCOUS IMPELLER ASSIST DEVICE AND METHOD.

This permanent pump concept in some embodiments is based a spinning disk configuration in the shape of a 2-sided centrifugal pump. For some embodiments of the permanent pump disclosed here, however, the impeller can be rigid: It is not required to expand (open) and contract (close). The rotating impeller (40), suspended in the midst of the housing (22), draws fluid in from the axial direction by way of inlets 23a (superior and inferior vena cava) and pumps it to the outlets (23b) which lead to the left and right lungs. A single pump effectively produces a 4-way pumping action which is useful to augment Fontan TCPC flow. Preliminary designs have been demonstrated and published to induce pressure differential of 2-10 mmHg in the nominal operating range (3-7K RPM, with capabilities of generating higher pressure (up to 40 mmHg) at higher rotational speeds in the unlikely event of pulmonary hypertension). Further, the pump has no potential to obstruct flow in the Fontan venous pathway. Even when non-rotational, the impeller continues to serve a streamlining function to passive flow through the TCPC, reducing the hydraulic energy loss within the 4-way junction.

Figure 1B:
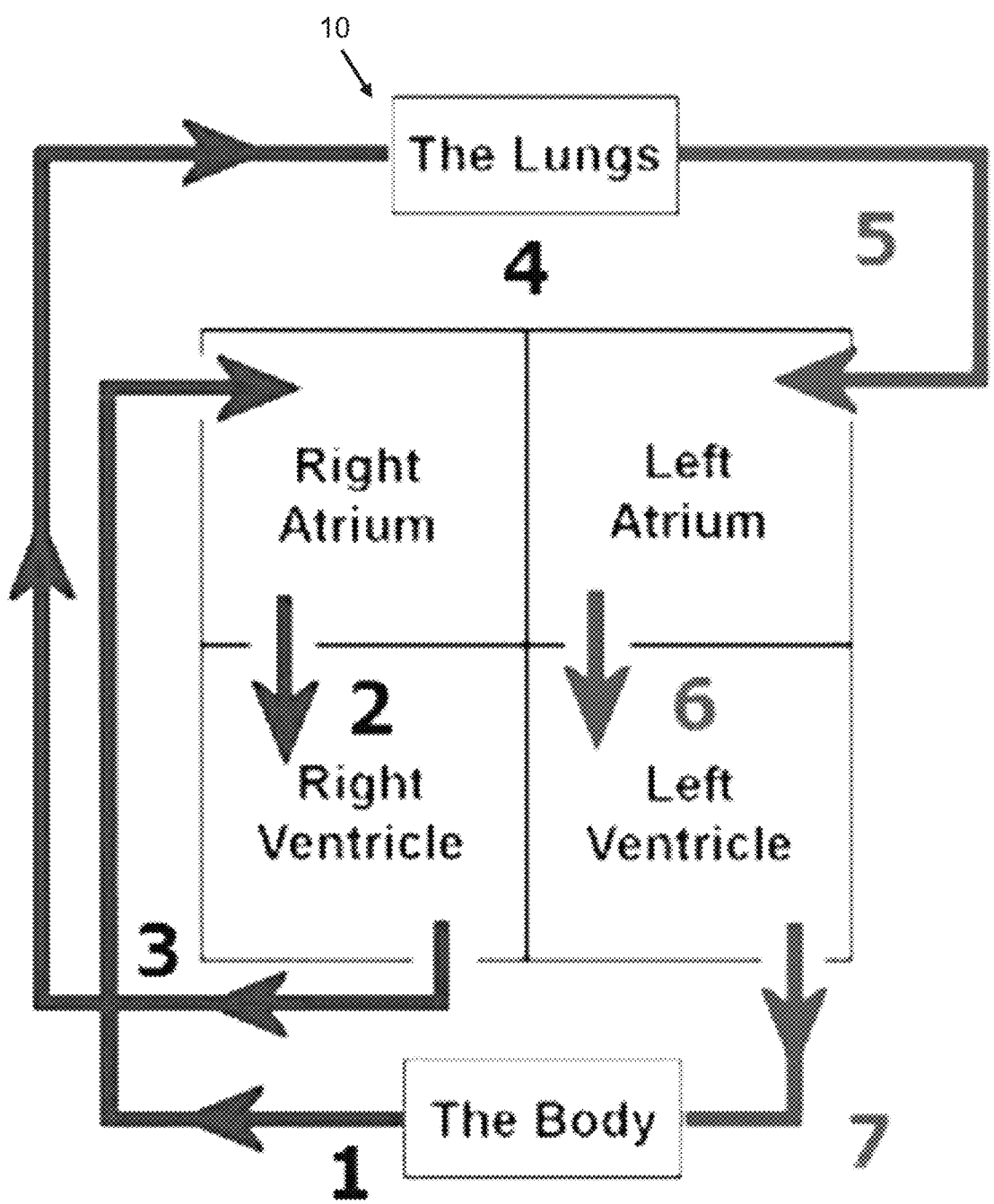
FIG. 1B is another schematic representation of the human circulatory system, presented in block diagram format.

FIGS. 1A and 1B depict schematic representations of the circulatory system of a human being. Various embodiments of the present invention pertain to such circulation systems, as well as to circulatory systems of any biological unit.

Figure 2C:
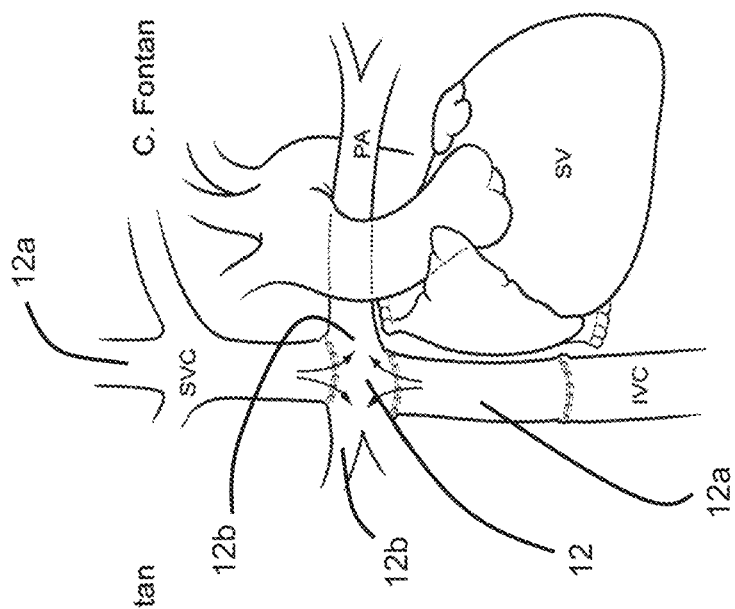
FIG. 2C is a schematic representation of a known surgical method.
Figure 2B:
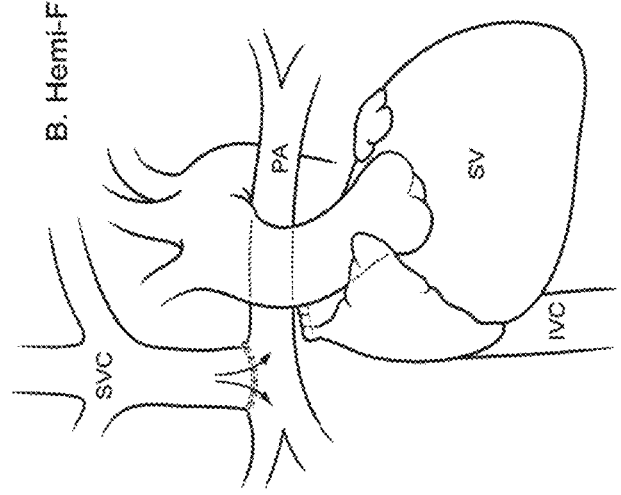
FIG. 2B is a schematic representation of a known surgical method.
Figure 2A:
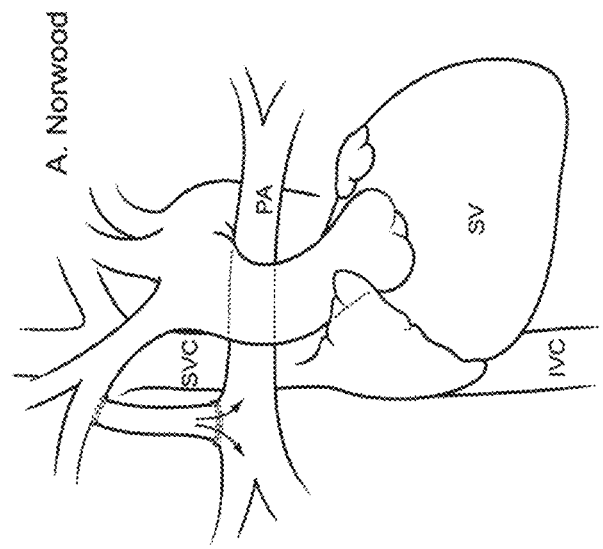
FIG. 2A is a schematic representation of a known surgical method.

FIGS. 2A, 2B, and 2C depict various reconstructions of a human circulatory system as modified by the Norwood, Hemi-Fontan, and Fontan procedures.

Figure 3A:
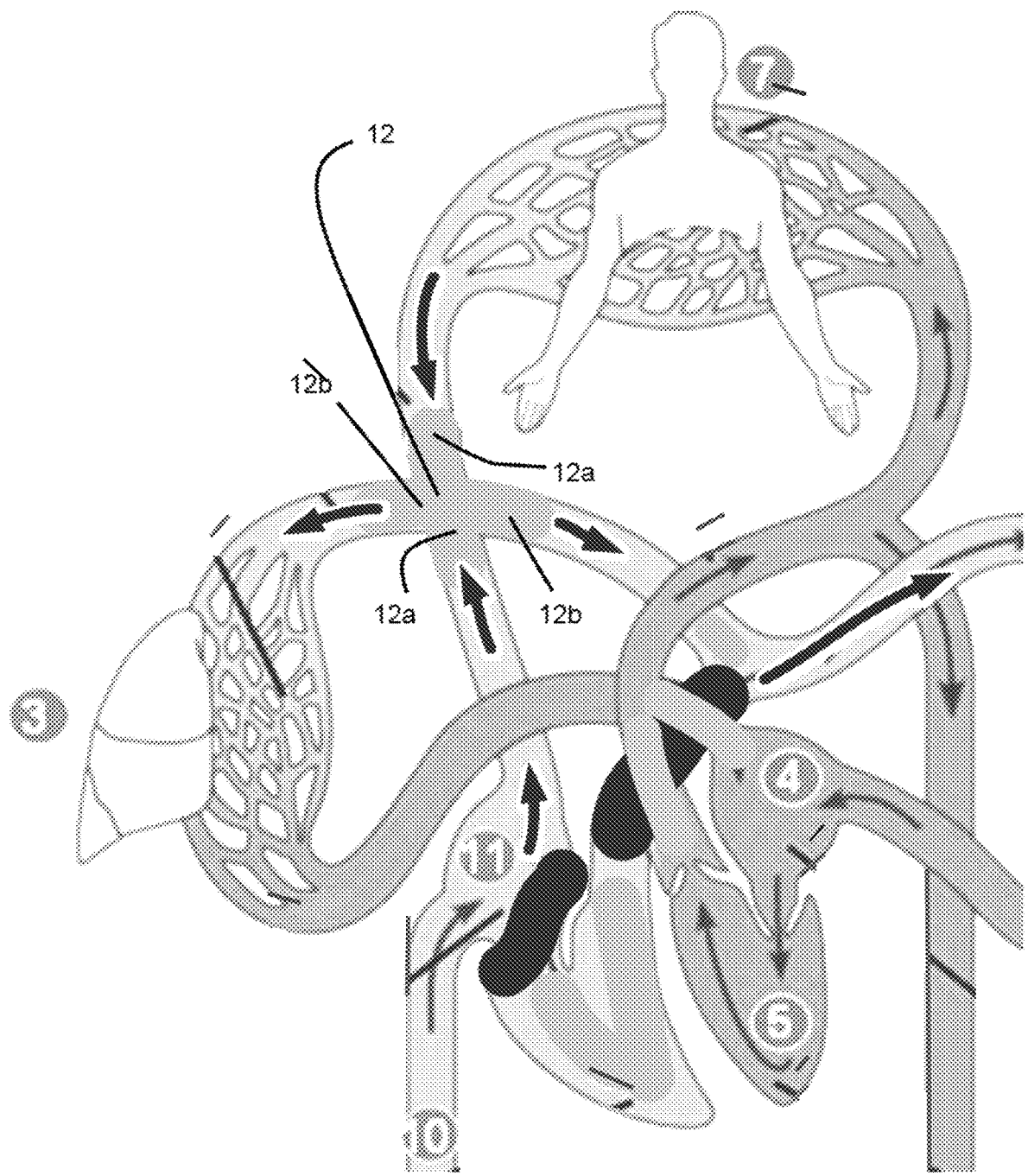
FIG. 3A shows the circulatory schematic of FIG. 1A as modified by the Fontan procedure of FIG. 2C.
Figure 3B:
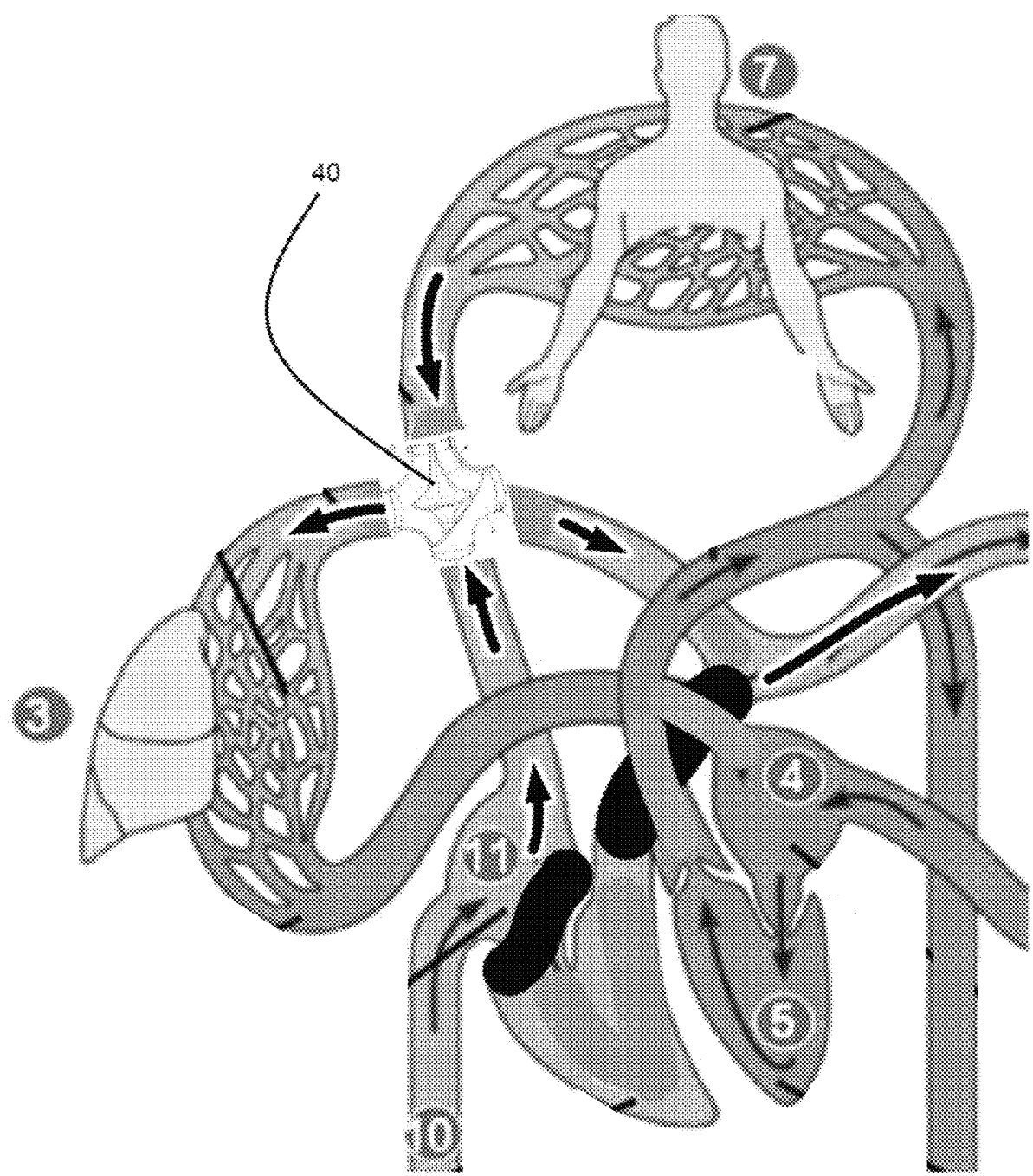
FIG. 3B shows the circulatory schematic of FIG. 3A with housing including a pumping element inserted at the Fontan junction.

FIG. 3A is a schematic representation of FIG. 1A, showing the surgical modification of FIG. 2C. FIG. 3B shows the system of FIG. 3A after an implantable impelling device 40 has been placed in the Fontan junction.

Figure 4A:
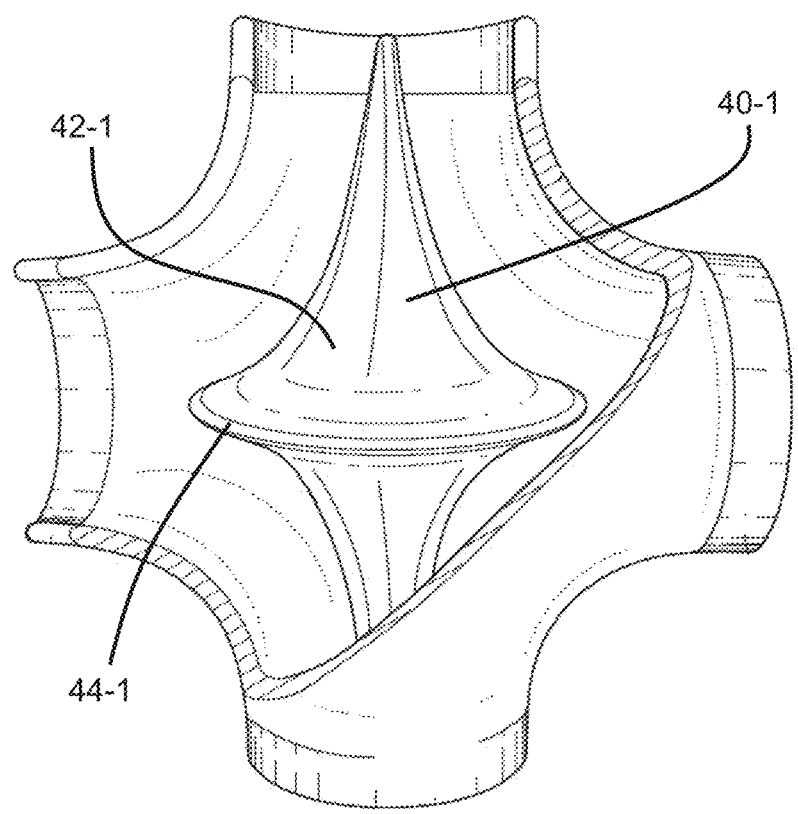
FIG. 4A is a CAD surface perspective representation, partially cutaway, of the housing and viscous impelling pump shown in FIG. 3B.
Figure 4B:
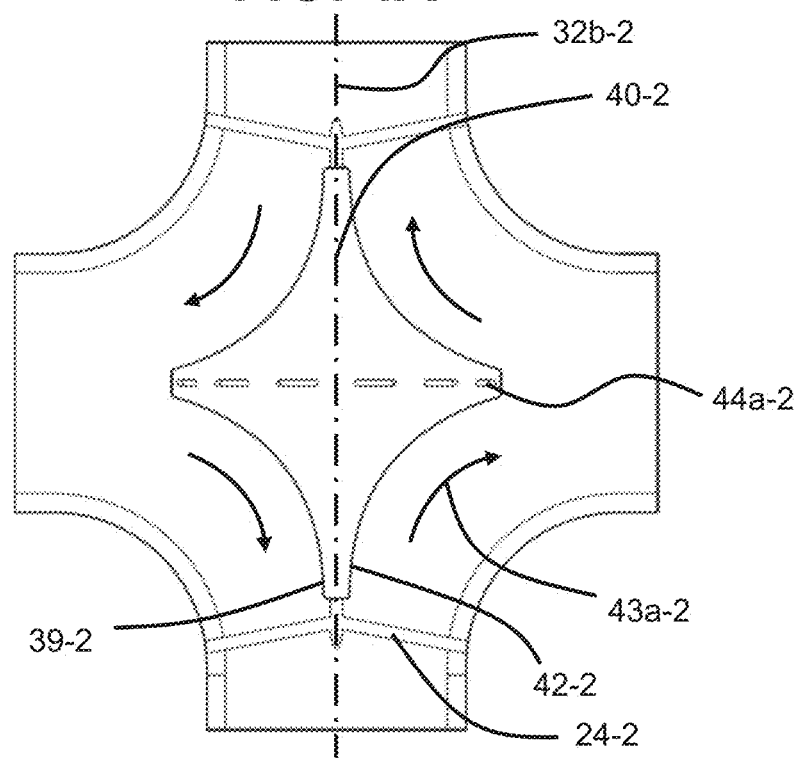
FIG. 4B is a side elevational CAD surface representation of a housing and pumping element useful in the modified circulatory system of FIG. 3A.
Figure 4C:
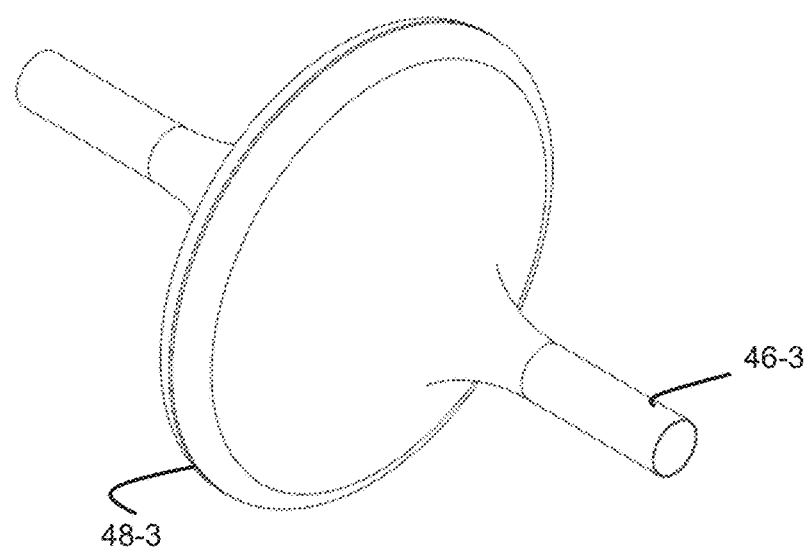
FIGS. 4C and 4D are perspective and side elevational views, respectively, of a pump useful in the Fontan-reconstructed circulatory system of FIG. 3A.
Figure 4D:
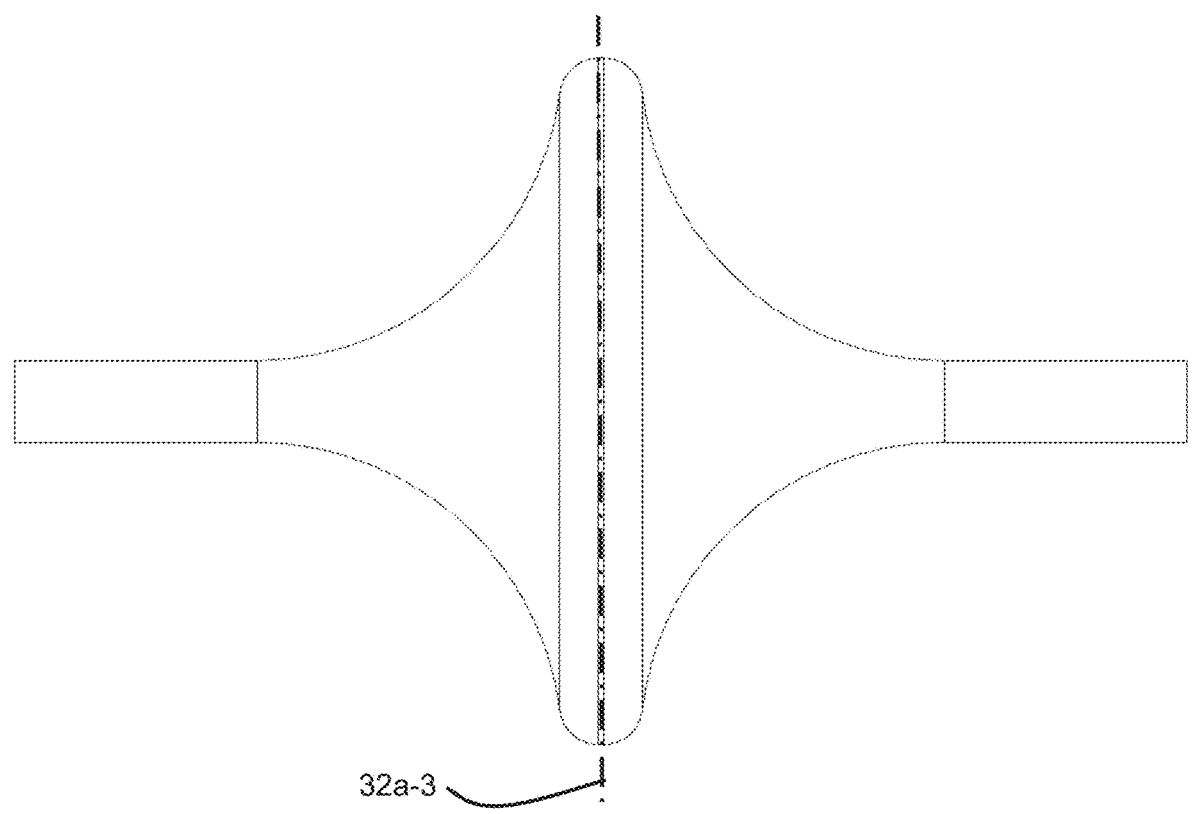
Figure 4E:
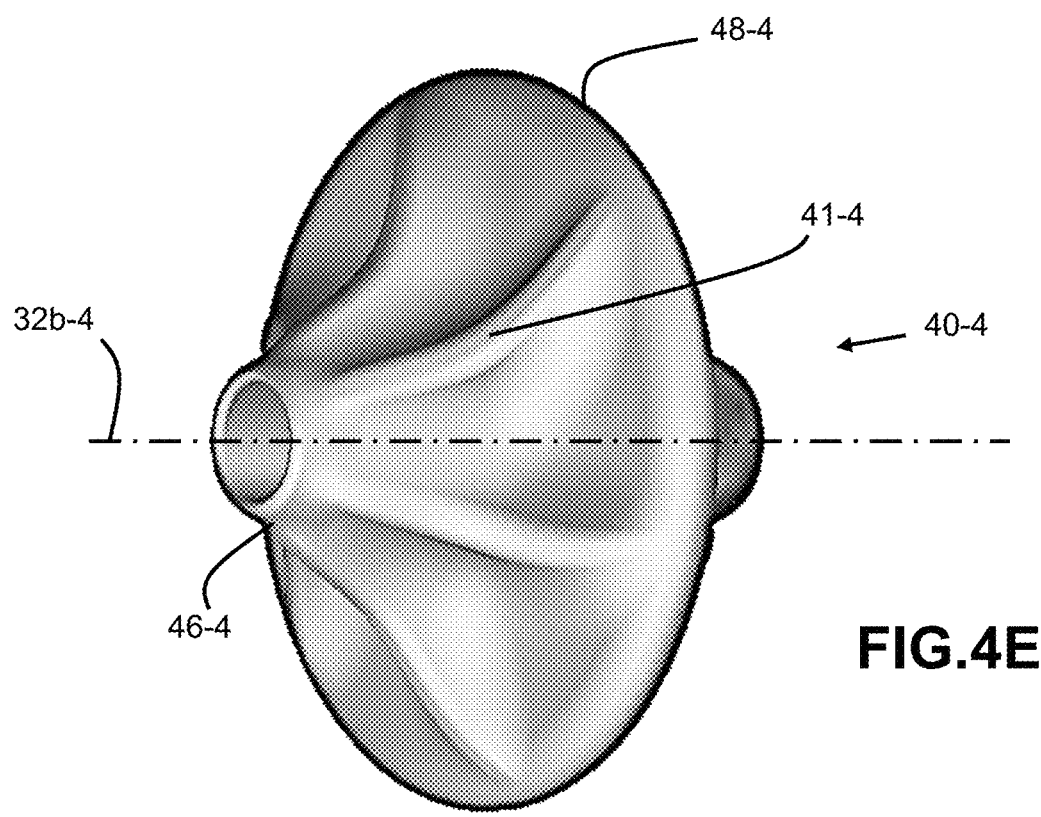
FIG. 4E is a surface-shaded CAD representation of a perspective view of one side of a viscous impelling pump useful in the Fontan-reconstructed circulatory system of FIG. 3A.
Figure 4F:
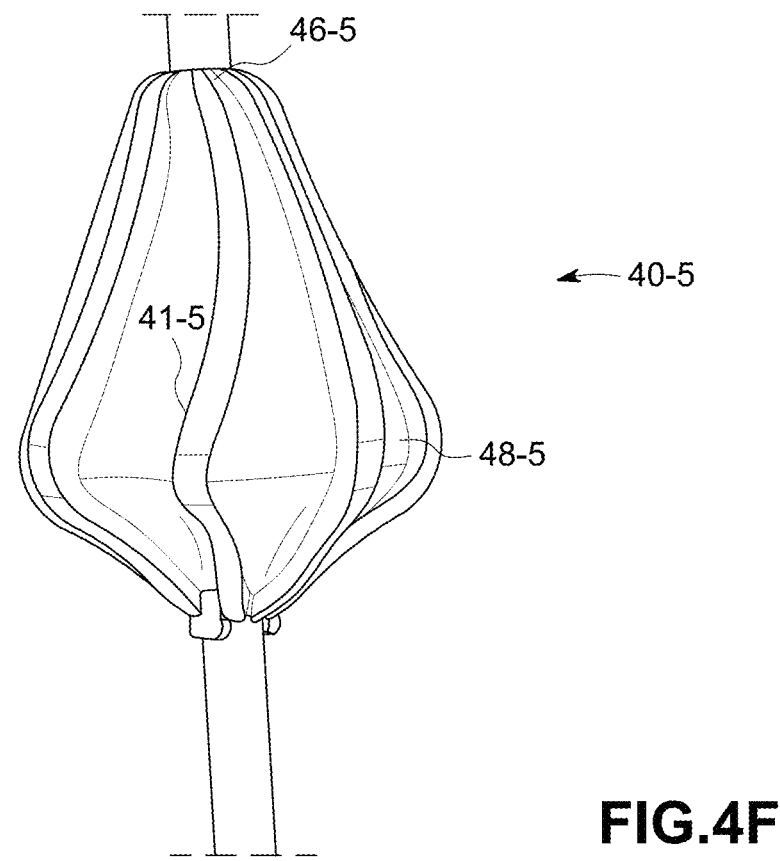
FIG. 4F is a side elevational photographic representation of a pump useful in a Y-shaped artery according to yet another embodiment of the present invention.

The housing 22 and nested impeller 40-1 of FIG. 3B are shown in FIG. 4A. FIGS. 4B, 4C, 4D, 4E, 4F, 4G, and 4H each depict alternative configurations of impellers 40-2, 40-3, 40-4, 40-5, 40-6, and 40-7. Each of these impellers 40-X provides increased energy to fluid flowing over the impeller by means of rotation of the impeller. The various impellers depicted herein can include rotating impeller blades similar to rotating compressor blades, having a curving nature that pushes flow in the direction of rotation of the impeller. Yet others have generally smooth surfaces that impart rotational energy to a flowing fluid by means of viscous drag. Still further impellers contemplated for the invention described herein contemplate combinations of smooth, viscous impelling surfaces and impelling blades. Further description of these devices can be found in the PCT applications referenced herein, with applicability as persons of ordinary skill in the art would recognize.

Figure 5A:
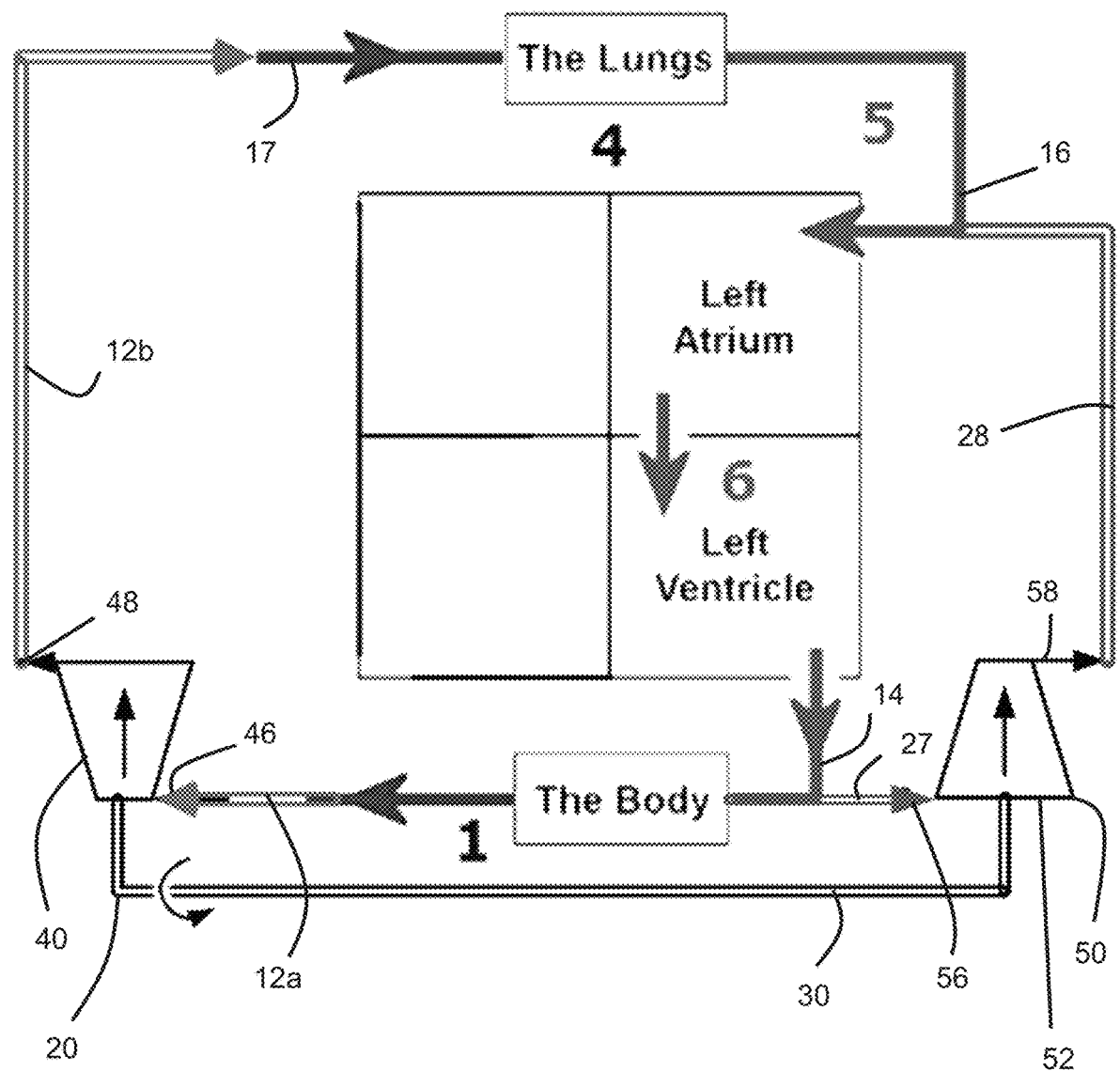
FIG. 5A is a schematic block diagram of a circulatory system with a Fontan modification, and including a motor-driven pump according to one embodiment of the present invention.

FIG. 5A is a schematic block diagram representation of a circulatory system that has been modified with a Fontan reconstruction. The circulatory system shown in FIG. 5A includes an implantable self-powered pumping device 20 that includes an impeller 40 and hydraulic motor 50 interconnected by a body 30. As previously discussed with regards to FIG. 3B, the impeller 40 receives blood from a Fontan junction source 12a at an impeller inlet 46. The rotating impeller 40 imparts energy to this flow of blood and provides the higher energy flow at an impeller outlet 48 and into the Fontan receiving passageways 12b.

FIG. 5A shows that blood from a first source (the left ventricle) has a first portion provided to the inlet of hydraulic motor 50, and the remaining portion provided to a first subsystem or restriction represented as the body, and including the systemic circulatory system of blood vessels and veins. The remainder portion flowing out of the body is provided to the inlet of a pump 40, which is rotated by a mechanical interface with the motor 50. The remainder portion exits the pump at a higher pressure than the pump inlet pressure, and is thereafter provided to a second subsystem or restriction of the circulatory pulmonary system (the lungs). As the remainder portion of flow passes through the lungs, it exits the lungs at a lower pressure (see region 5 on FIG. 5A), where it is placed in fluid communication with the portion of the flow from the left ventricle that exited from the outlet of the hydraulic motor. The blood flowing from the exit of the hydraulic motor is in fluid communication with the blood exiting the lungs. Although what has been shown and described is an overall fluid system that incorporates one or more restrictions or subsystems, it is understood that yet other embodiments of the present invention contemplate overall fluid systems comprising means for hydraulically powering a centrifugal pump, and means for centrifugally pumping a fluid.

In a preferred embodiment, the impeller 40 is integrated with a hydraulic motor 50 on a unitary body 30. It is understood that in some embodiments, body 30 is fabricated from separate parts, and in still further embodiments those separate parts are preferably integrated together by way of adhesive, ultrasonic welding, brazing, or the like. In still further embodiments a unitary body 30 is fabricated from one or more parts fabricated by way of additive manufacturing, such as 3D printing.

Figure 5B:
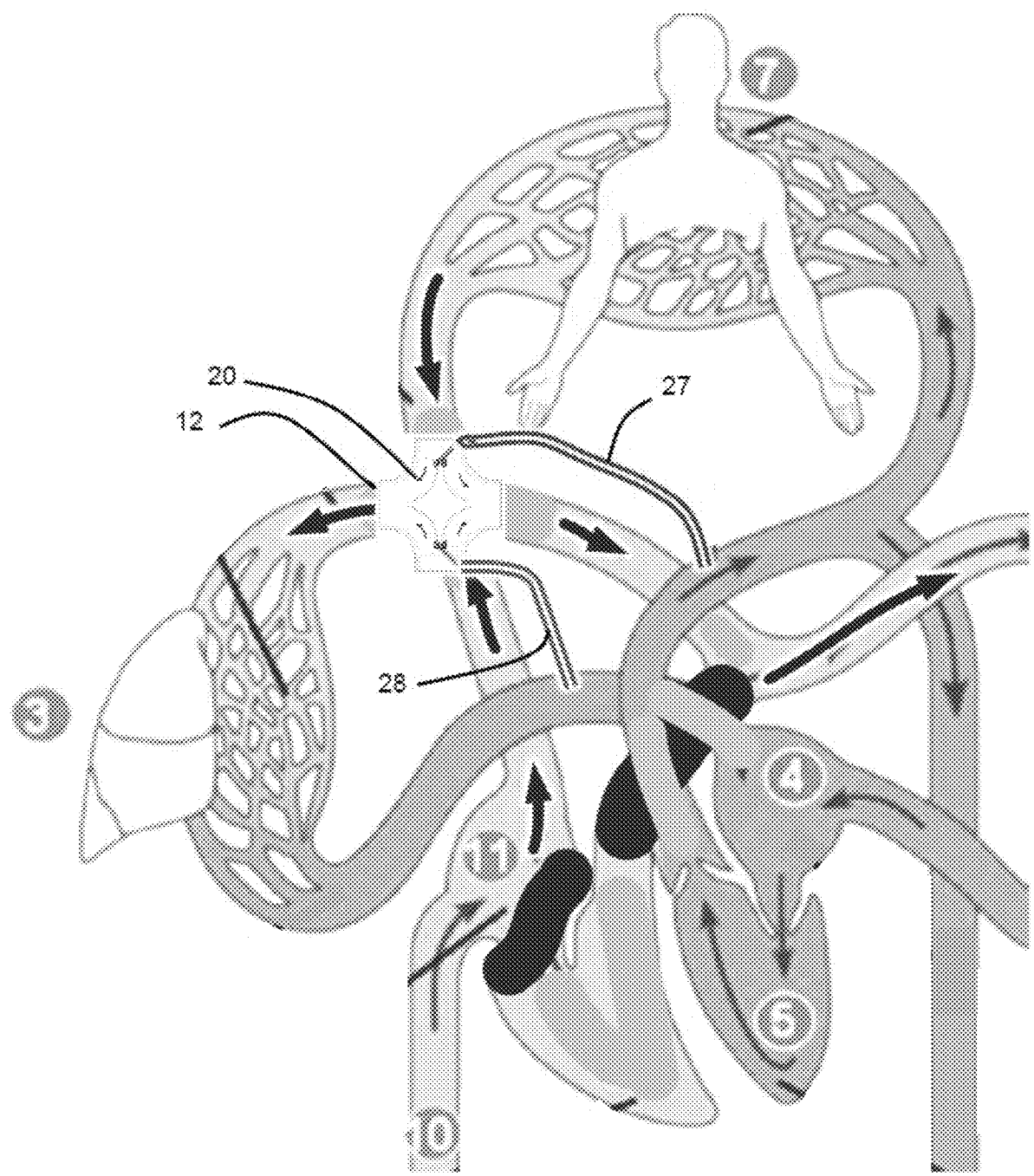
FIG. 5B is a schematic representation of a human circulatory system with a Fontan modification, using an implanted motor and pump according to another embodiment of the present invention.

The motor 50 of implantable device 20 includes motive conversion features 55 that convert energy from a blood supply 14 from the output of the left ventricle into rotary power, and uses this kinetic energy to impart spin to body 30 and impeller 40. After the conversion from hydraulic power to rotational mechanical power, the blood leaves the motor exit 58 and returns to the blood 16 being supplied to the left atrium. Blood flow from the left ventricle to the motor is provided by way of a supply shunt 27, and the motor return flow is provided to the left atrium by a return shunt 28, as best seen in FIG. 5B.

Figure 6:
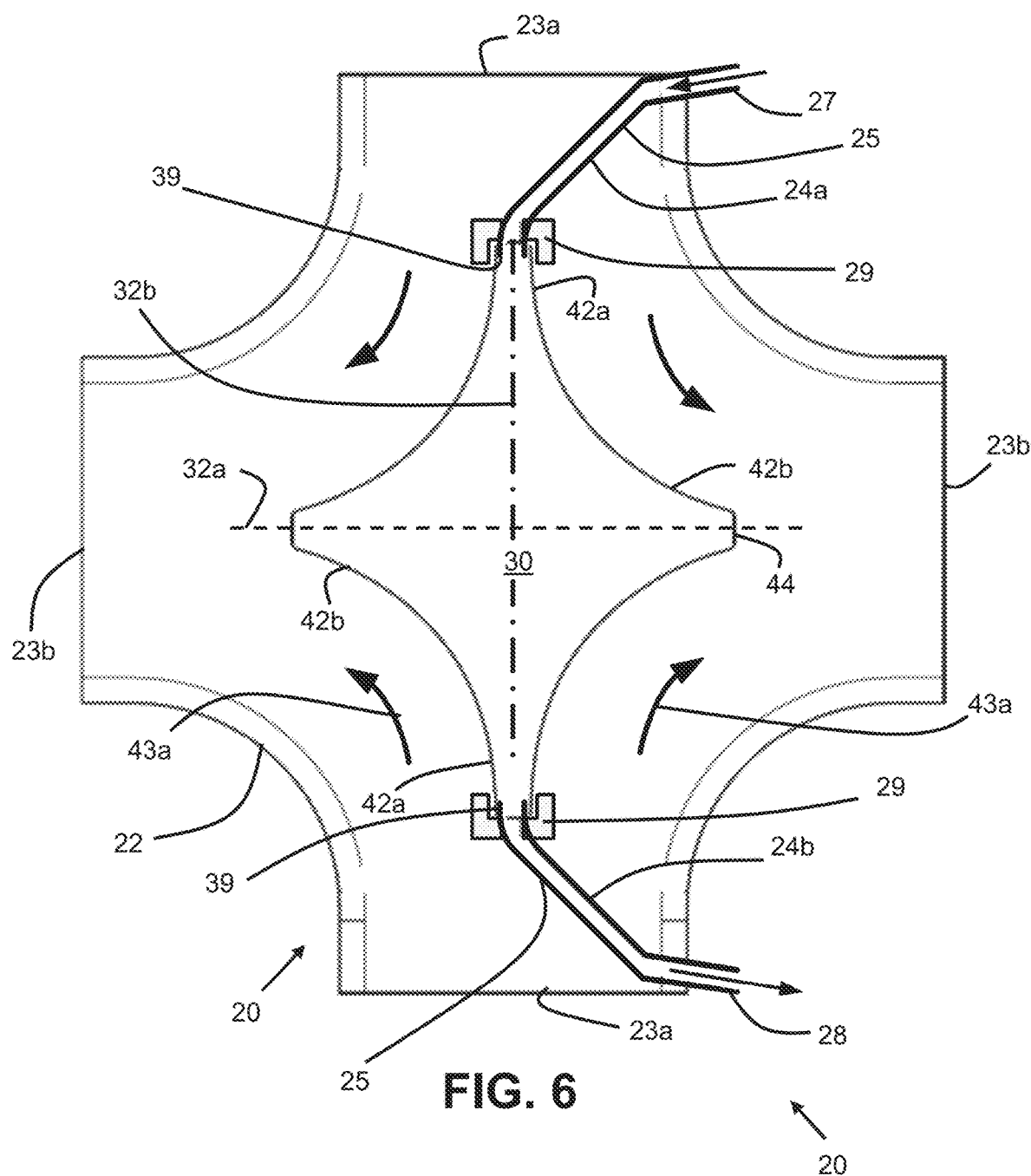
FIG. 6 is a side elevational, partially cutaway representation of the motor-driven pumping element of FIG. 5B, and shown mounted in a housing.
Figure 7:
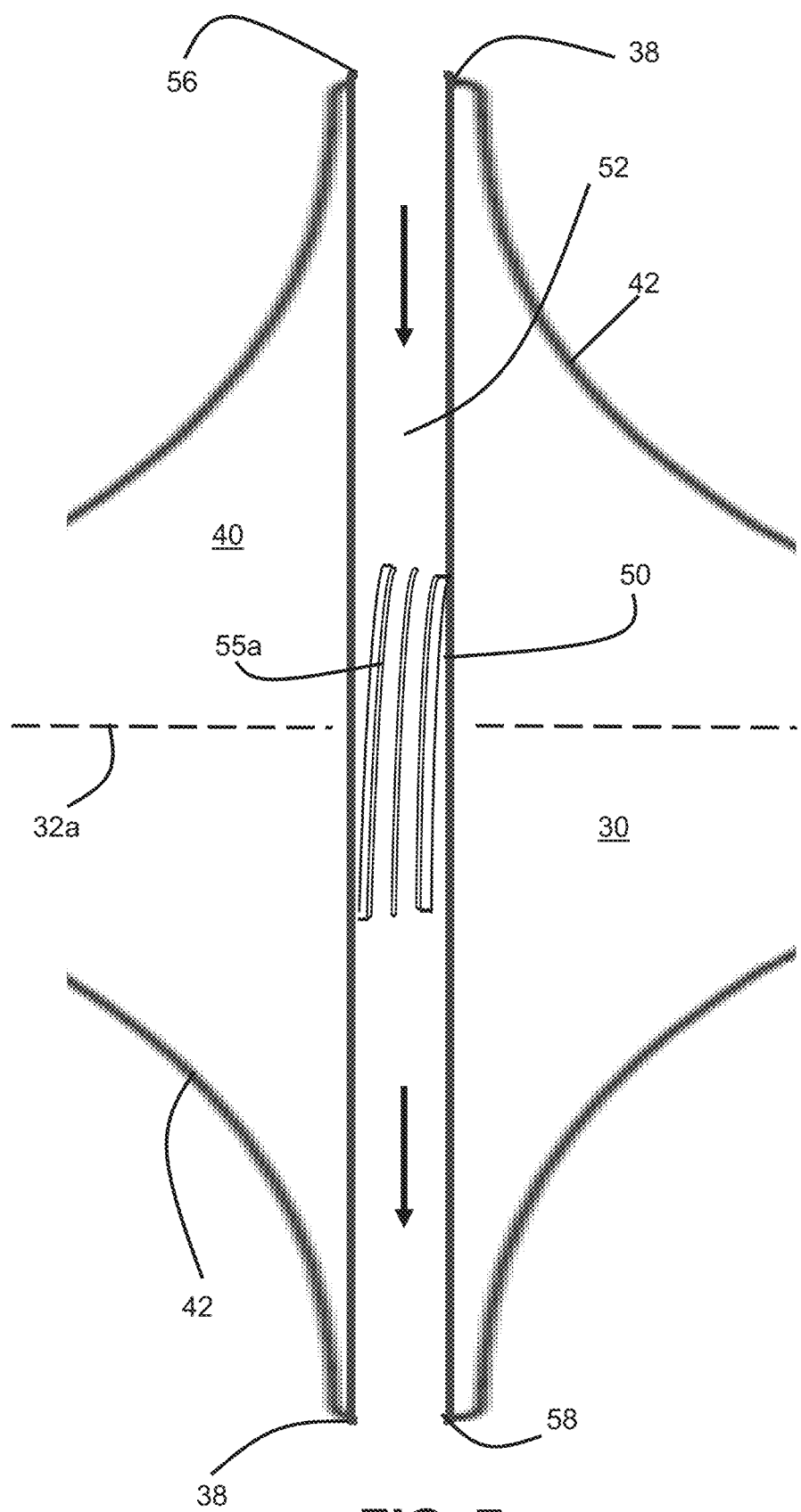
FIG. 7 shows an enlarged cutaway of a portion of the apparatus of FIG. 6.
Figure 8:
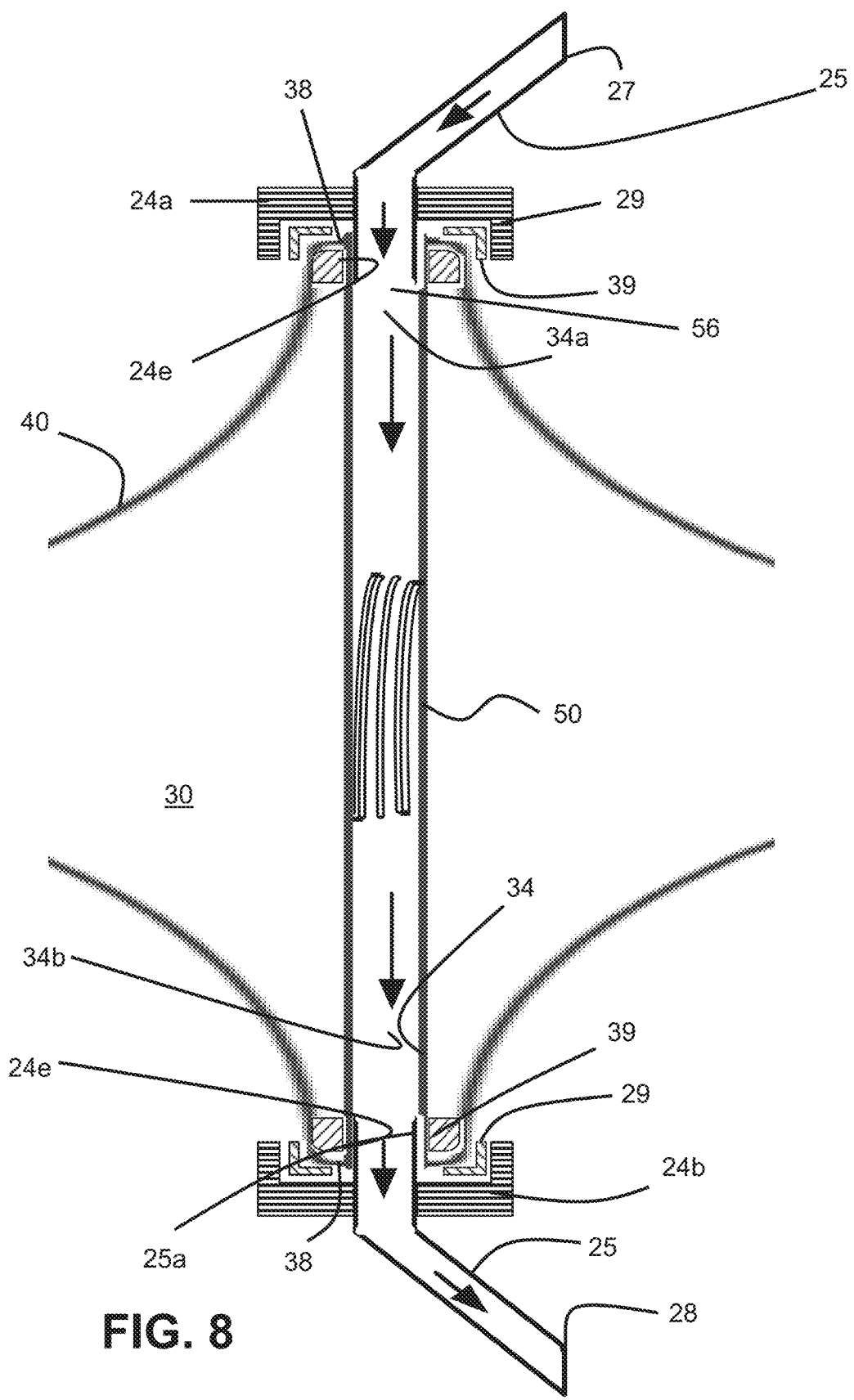
FIG. 8 shows a cutaway schematic representation of a portion of a motor-driven pumping apparatus according to another embodiment of the present invention.

FIGS. 6, 7, and 8 show various features provided in some embodiments of device 20. FIG. 6 shows a cutaway of the housing 22 that includes inlets 23a that receive blood from the Fontan junction sources 12a. Housing 22 further includes a pair of outlets 23b that are in fluid communication with the receiving pathways 12b of the Fontan junction. Although what is shown and described is a device 20 having dual, opposing inlets oriented generally perpendicularly to a pair of dual, opposing outlets, yet other embodiments are not so constrained. As will be discussed with regards to FIGS. 16 and 17, yet other embodiments contemplate a single inlet with dual outlets (such as in a Y-shape or a T-shape). Still further embodiments contemplate housings having a single inlet and single outlet.

Housing 22 further includes a pair of stationary support structures 24 that locate body 30 within housing 22. Supports 24 each include a stationary bearing 29 that establishes a rotating interface with a rotating bearing 39 located proximate to the supported end 38 of body 30. Preferably, stationary bearings 29 further include features that establish the location of rotor 30. As shown schematically in FIG. 6, static bearings 29 can have a cup-type shape, in which the supported end 38 is received within the depression of the cup, with the walls of the cup preventing escape of the body supported end 38 from the depression.

Supports 24 further include an internal flowpath that provides blood under pressure to motor 50. A supply shunt 27 couples to the fluid inlet 24a located within a strut. The hollow strut extends a short distance into passageway 34, as best seen in FIG. 8. This overlap of extension 25a into the passageway 34 forms an outer annular area that is adapted and configured to discourage leakage from passageway 34 to the exterior of body 30. However, in some embodiments the annular interface between extension 25a and passageway 34 includes one or more sealing devices that further discourage leakage flow of the higher pressure blood from passageway 34 into the blood within the Fontan junction.

FIGS. 7 and 8 further show the motive conversion features 55 of motor 50. As previously described, motor 50 is of the closed flowpath type 52 in which blood from an inlet shunt 27 flows within passageway 34, and out a return shunt 28 to another part of the circulatory system. With this closed architecture, the blood used to provide motive flow is discouraged from mixing with blood within the Fontan junction. Referring again to FIG. 7, it can be seen that the blood flowing from motor inlet 56 to motor outlet 58 passes over one or more motive conversion features that use the flowing blood to impart rotational energy to rotor 30. Motor 50 includes a plurality of elongated blades 55a that have a shape adapted and configured to include a higher pressure surface upon which the higher pressure blood flows. In any of the motive features discussed herein, the features 55 can be adapted and configured to utilize the inertia of the flowing blood to impart rotational energy (impulse type), the pressure of the blood to impart rotational energy (reaction type devices), or combinations of the same. Motor features 55 discussed herein include any of the features associated with rotational hydraulic motors, including, as examples, the features associated with Pelton, Kaplan, and Francis fluid turbines. Further examples of the motive features can include any of the features and flow systems associated with radial inflow turbines or radial outflow turbines.

The elongated blades 55a of motor 50 are preferably configured to include a higher pressure surface on one side, and a lower pressure surface on the other side of the blade. This pressure differential integrated over the entire surface area of the blade provides a force to body 30. A component of this force is perpendicular to rotational axis 32b, and since the net force is exerted a distance from the rotational axis, a torque is applied to body 30. The elongated blades in some embodiments have a shape that at least partially spirals around the inner diameter of the flow passageway 34. As will be discussed with regards to device 120 and shown in FIG. 10, the spiral shape preferably has a limited radial extent, and the blades 55a leave open a largely unobstructed central passage similar to that of central passage 134c of FIG. 10.

The net pressure force acting on any of the individual elongated blades 55a further includes a vector component oriented parallel to the rotational axis. In some embodiments, this parallel vector component results in a net axial force that pushes rotor 30 in a direction along the axis. For the orientation shown in FIG. 7, this net axial force would push rotor 30 toward motor outlet 58.

The motive conversion features 55 shown in FIG. 7 are only those features extending from the bottom third of the passageway 134 toward the center. It is understood that these motive conversion features are provided around the entire internal periphery of flow passage 134. Further, preferred embodiments of the present invention contemplate placement of the motive conversion features along the length of the rotational axis so as to establish rotor 30 as being dynamically balanced by design. However, it is contemplated that rotors according to various embodiments of the present invention may have their operation enhanced by dynamic balancing of the rotor after fabrication.

The embodiment shown in FIG. 8 includes an arrangement of magnetic bearings at each supported end of the rotor 30. Shown schematically in FIG. 8, rotor 30 includes a rotating magnetic bearing 39 located proximate to supported end 38. This permanent magnet interacts with a ring shaped static bearing 29 (shown as an L-shape in cross hatch) that is secured to the support 24. Preferably, each supported end 38 of rotor 30 includes magnet bearings to discourage contact between rotor 30 and static support 24. It is understood that in some embodiments in which motor 50 exerts a net axial force, that the magnetic bearings on one end can be sized appropriately for a heavier axial load, whereas the magnetic bearings on the opposite supported end (such as near the inlet 56 in FIG. 8) can be adapted and configured for the different (lower) axial load.

Although what has been shown and described is a rotor supporting system and methodology that utilizes magnetic bearings, yet other embodiments of the present invention contemplate still further means for accommodating the net axial load of the motor. As another example, the external shape and outer surface 42 of impeller 40 can be adapted and configured to provide a net axial force that acts in a direction opposite to that resulting from motor 50. Referring to FIG. 6, in some embodiments the external shape 42 of rotor 30 is symmetric about a midplane 32a, as well as being axisymmetric about rotational axis 32b. This external shape 42 of impeller 40 results in a generally balanced rotor, with no net axial force resulting from the viscously impelled external flow 43. Flow from the inlets 23a extend evenly and uniformly about the impeller surface inlets 42a, and likewise flow smoothly and uniformly over the outlets 42b located proximate to apex 44.

However, this shape can be altered, and in some embodiments the outer shape 32 of body 30 is not symmetrical about a midplane. As one example, the outlet shape 42b on the bottom side of the rotor (referring to FIG. 6) can be altered to provide more flow than the top half of the rotor. In such embodiments, the additional flow from the bottom half of the rotor would likewise impart additional viscous drag along the inlet 42a of the bottom half (exceeding the inlet drag on the inlet portion 42a of the top half), resulting in a net axial force upward (referring to FIG. 6) in such embodiments. Therefore, the shape of impeller 40 cab be altered to provide a net axial force from pumping that opposes the net axial force from the motor.

FIGS. 9 and 10 depict a portion of an implantable pumping device 120 according to another embodiment of the present invention. Device 120 includes a body 130 rotatable suspended within a housing 122 (not shown) by one or more supports 124 on each supported end 138. Body 130 includes an impeller 40, a portion of the impeller being shown in FIG. 9.

It can be seen that motor 150 is of the closed flowpath 152 type, with flow from a supply shunt 27 being provided to the inlet 134a of a motive flow passageway 134. The flow in passageway 134 passes over one or more motive conversion features 155, flowing toward an exit 134b proximate a suspended end 138 of rotor 130. The exit flow leaves device 120 by way of a strut 125 (not shown), and finally through a return shunt 28 (not shown). It is understood that other features (such as the stationary and rotating bearings, the overlapping strut extension, and others) can be of any type shown herein, but are not shown in FIG. 9 for purposes of clarity.

Motor 150 includes a plurality of bucket-shaped devices 155c that are adapted and configured to convert fluid energy from the flowing blood into rotational energy of rotor 130 by way of an impulse turbine. Preferably, each of the buckets 155c are curved with a concave side that receives flow within passageway 134. FIG. 10 shows a system of devices 155 arranged in a plurality of rows extending over a predetermined length of passageway 134.

FIG. 10 presents an end view of the rows of buckets 155c, with the planform of the buckets being projected orthogonally along the rotational axis in the end view. It can be seen that the buckets extend completely around the inner periphery of pathway 134. Each bucket is preferably of a height that does not extend to the centerline (rotational axis) of rotor 130. Instead, a substantially unobstructed central portion 134c is established within passageway 134. This free flowing passageway permits a flow of blood through passageway 134 with relatively limited pressure drop, even if the rotor 130 were to stop rotating. In this manner, in the event of the failure of device 120, blood is still able to flow from shunt 27 to shunt 28. However, yet other embodiments of the present invention contemplate those embodiments in which the height of the devices 155 extend generally to the centerline of passage 134. Such embodiments contemplate an alternative failure theory, in which it is acceptable to discourage flow from shunt 27 to shunt 28, with this flow instead being encouraged from the left ventricle to flow to the remainder of the circulatory system of the biological unit.

Figure 11:
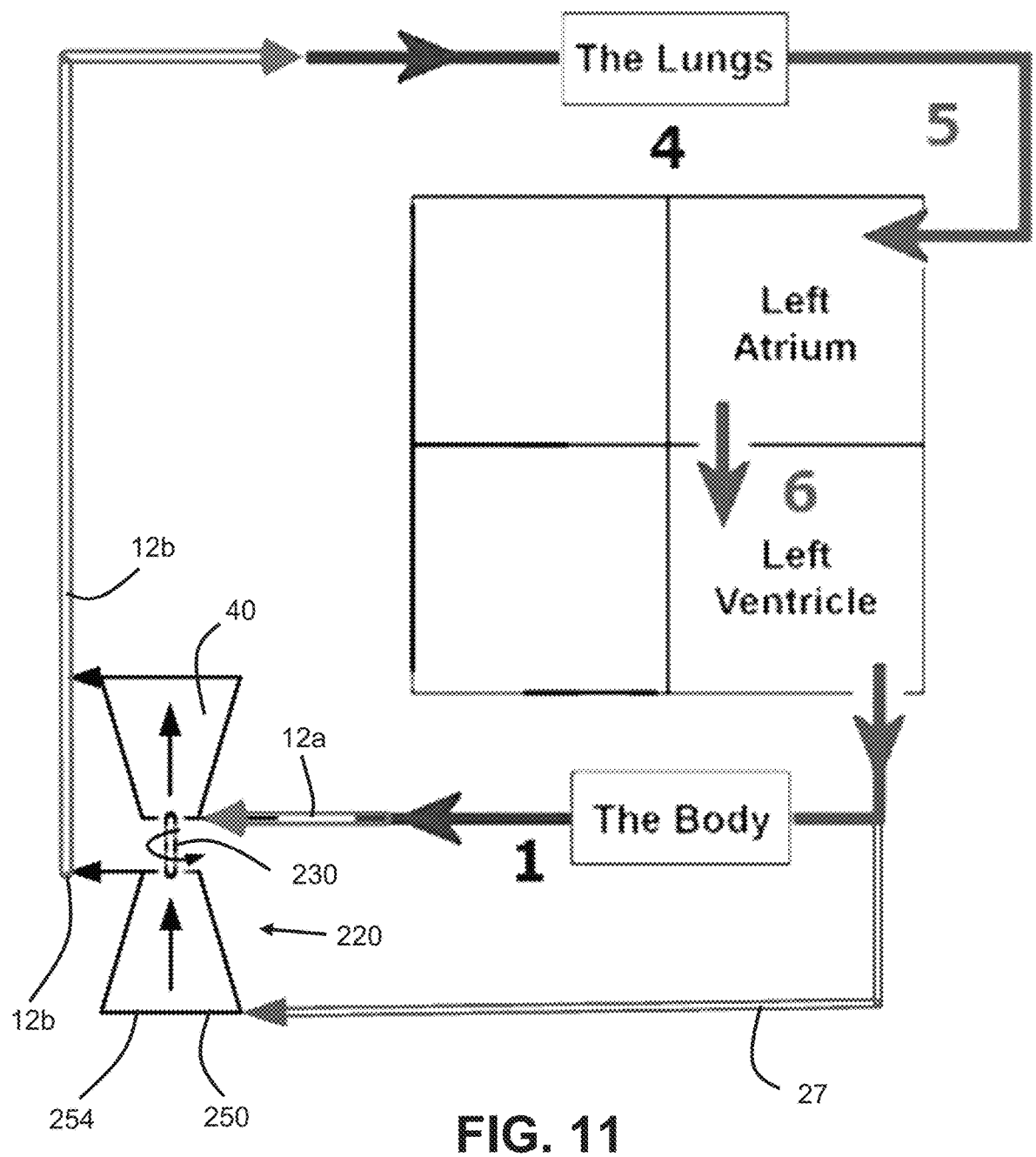
FIG. 11 is a schematic block diagram of a circulatory system with a Fontan modification, and including a motor-driven pump according to one embodiment of the present invention.

FIG. 11 shows a schematic block diagram representation of a circulatory system that has been modified with a Fontan reconstruction. The circulatory system shown in FIG. 11 includes an implantable self-powered pumping device 220 that includes an impeller 40 and hydraulic motor 250 interconnected by a body 230. As previously discussed with regards to FIG. 3B, the impeller 40 receives blood from a Fontan junction source 12a at an impeller inlet 246. The rotating impeller 40 imparts energy to this flow of blood and provides the higher energy flow at an impeller outlet 48 and into the Fontan receiving passageways 12b.

In a preferred embodiment, the impeller 40 is integrated with a hydraulic motor 250 on a unitary body 230. It is understood that in some embodiments, body 230 is fabricated from separate parts, and in still further embodiments those separate parts are preferably integrated together by way of adhesive, ultrasonic welding, brazing, or the like. In still further embodiments a unitary body 230 is fabricated from one or more parts fabricated by way of additive manufacturing, such as 3D printing.

The motor 250 of implantable device 20 includes motive conversion features 255 that convert energy from a blood supply 14 from the output of the left ventricle into rotary power, and uses this kinetic energy to impart spin to body 230 and impeller 40. After the conversion from hydraulic power to rotational mechanical power, the blood leaves the motor exit 58 and mixes with blood being pumped by impeller 40. Blood flow from the left ventricle to the motor is provided by way of a supply shunt 27, and the motor return flow is provided to either the impeller inlet or impeller outlet.

Figure 12A:
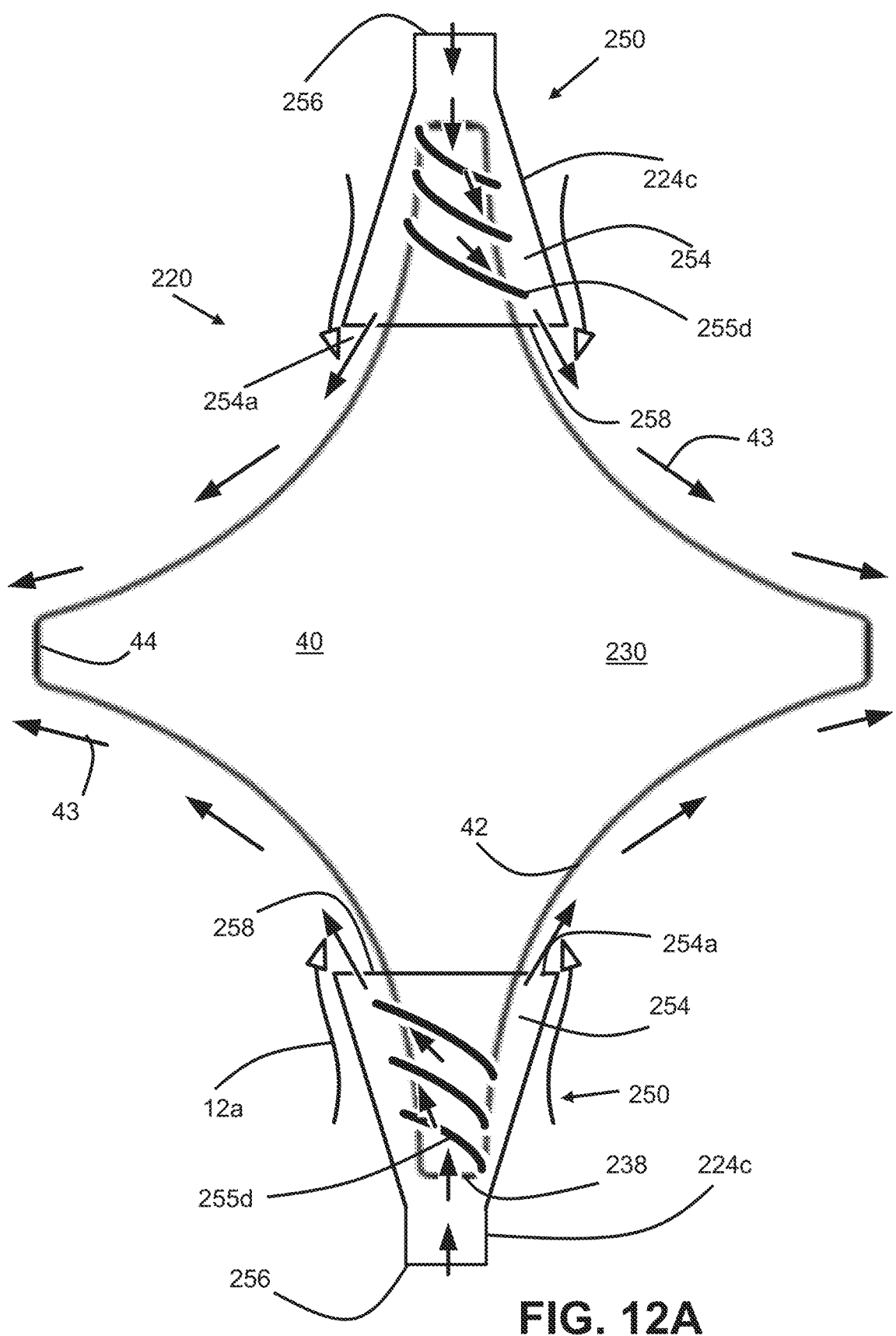
FIG. 12A is a side elevational portion of a schematic representation of a portion of a motor-driven pumping element according to another embodiment of the present invention.

FIG. 12A shows a portion of an implantable pumping device 220 according to another embodiment of the present invention. Device 220 includes a rotor 230 having an impeller 40 and a pair of hydraulic motors 250. A motor 250 is provided on each of the opposing supported ends 238. For sake of clarity, the bearings, struts, shunts, and other features are not shown, but it is understood that such features are contemplated. A single motor 250 will be described, although what is understood is that each of the motors 250 are identical, except that each are designed to rotate rotor 230 in the same direction when the two motors are located in facing opposition.

Motor 250 includes a spiral shaped motive conversion feature 255d that is located proximate to a supported end 238 of rotor 230. As indicated by the arrows, blood flowing into the motor inlet 256 reacts with the flow facing, curving, spiral shape of the conversion feature 255d, resulting in a net torque on body 230. Each motor includes an inlet shroud 224c that is attached to the support 224 (support not shown). The inlet shroud 224c receives flow from supply shunt 27 at an inlet 256. The shroud has a curved or conical shape that generally establishes a close-fitting annular passage between the inner surface of the shroud and the outer surface of the motor. The shroud increases the amount of work extracted from the inlet blood flow by maintaining this blood flow close to the rotating motive conversion features 255d.

Flow from inlet 256 flows over and around the motive conversion features 255d, and after imparting rotational energy to rotor 230, exits from the annular area 258 between the shroud exit and the outer surface 42 of the impeller. As this flow exits, it mixes with blood 12a from the Fontan source. These two flows (the external flow 12a over the exterior of shroud 224c and flow from supply shunt 27 within shroud 224c) mix in a mixing region 254a at the shroud exit. This mixture of flows is then influenced by the rotation of impeller 40, and proceeds along outer surface 42 toward apex 44, this mixed flow having increased total energy from the viscous impelling effect.

Figure 12B:
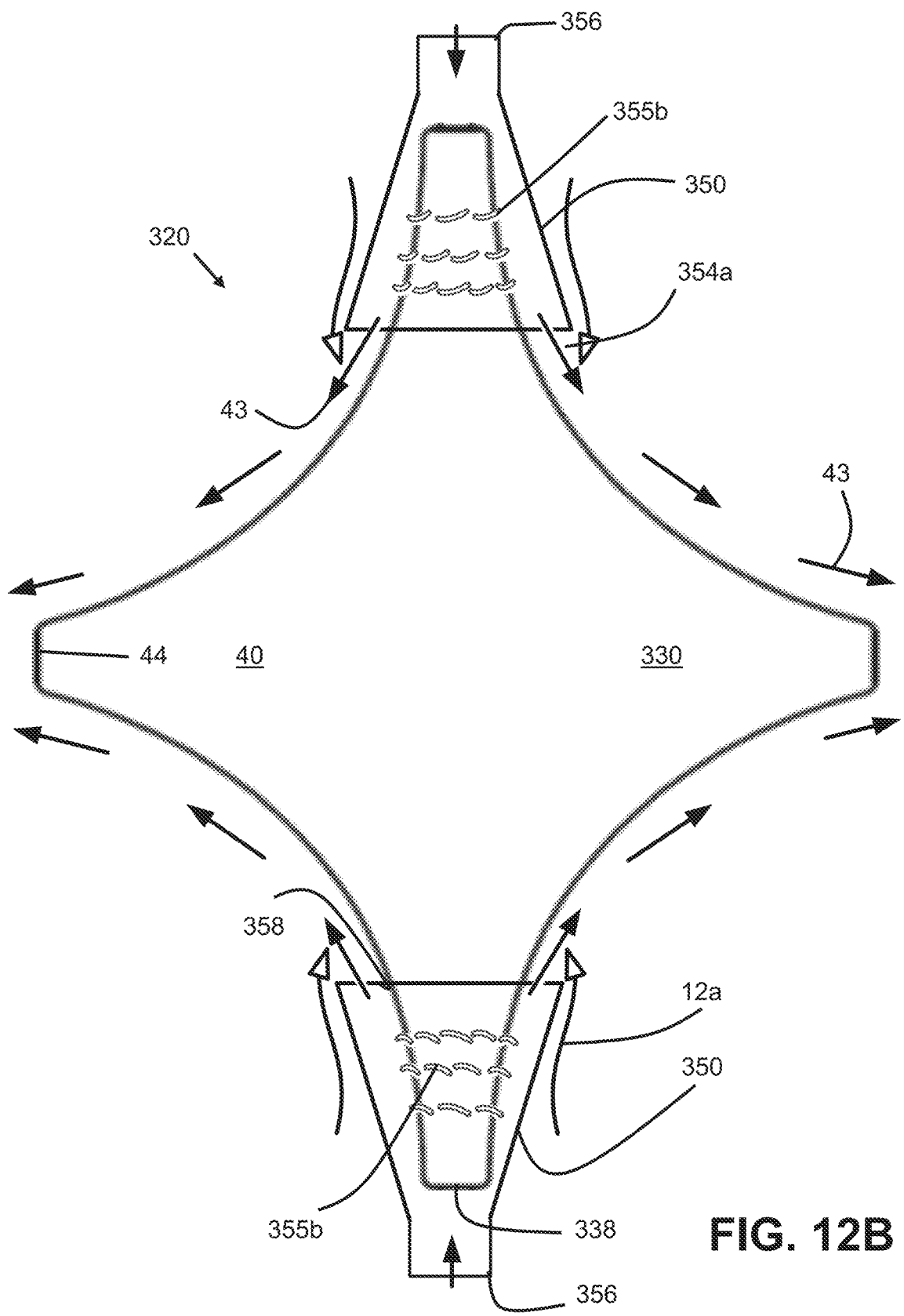
FIG. 12B is a side elevational portion of a schematic representation of a portion of a motor-driven pumping element according to another embodiment of the present invention.

FIG. 12B shows a similar portion of a device 320 that includes a rotor 330 having an impeller 40 and a pair of facing, opposed, motor 350. The operation of device 320 is similar to that described for device 230, except that motor 350 includes one or more motive conversion features 355b such as turbine blades. In some embodiments, adjacent turbine blades overlap, such that the leading edge of one turbine blade is in front of the trailing edge of the adjacent turbine blade, the two blades having exterior shapes such that the pathway between the backside of the front blade and the front side of the back blade create a pressure differential across a blade that causes the blade to have a net force on it. This net force creates a torque to rotate impeller 40.

Figure 12C:
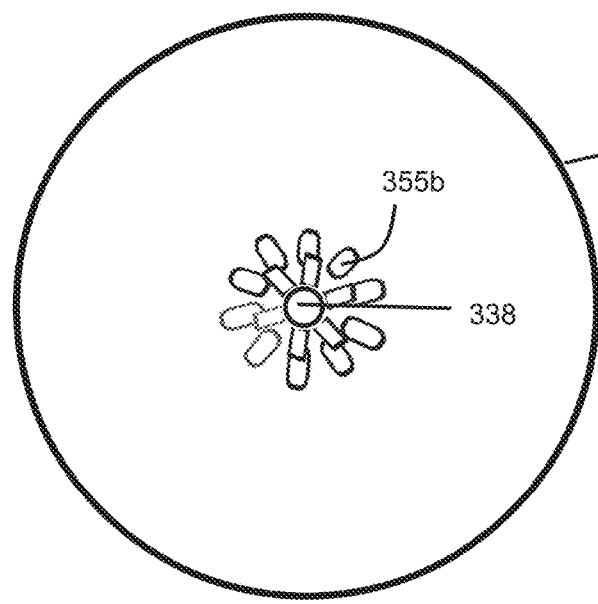
FIG. 12C is an end elevational view of a portion of the apparatus of FIG. 12B.

FIG. 12C shows an end view of the motor 350 of FIG. 12b, but showing only two rows of motive features 355b. It can be seen that each successive row of devices 355b is preferably populated with additional devices, so as to maintain acceptable spacing between adjacent blades as the outer diameter of surface 42 increase.

Figure 12D:
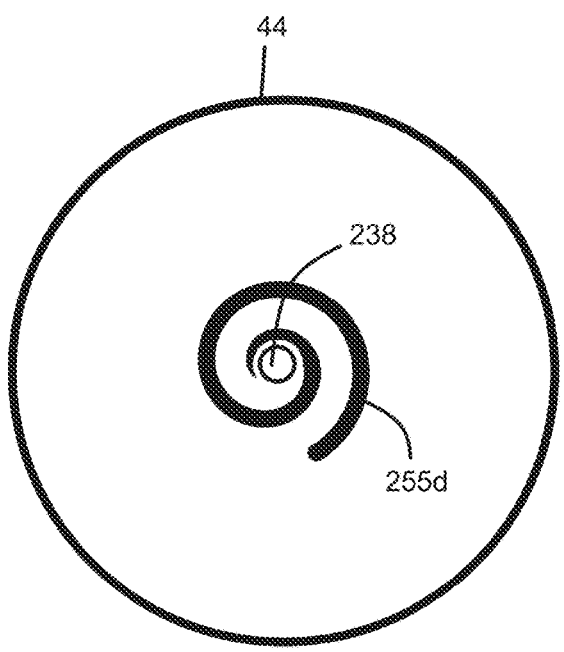
FIG. 12D is an end elevational view of a portion of the apparatus of FIG. 12A.
Figure 12F:
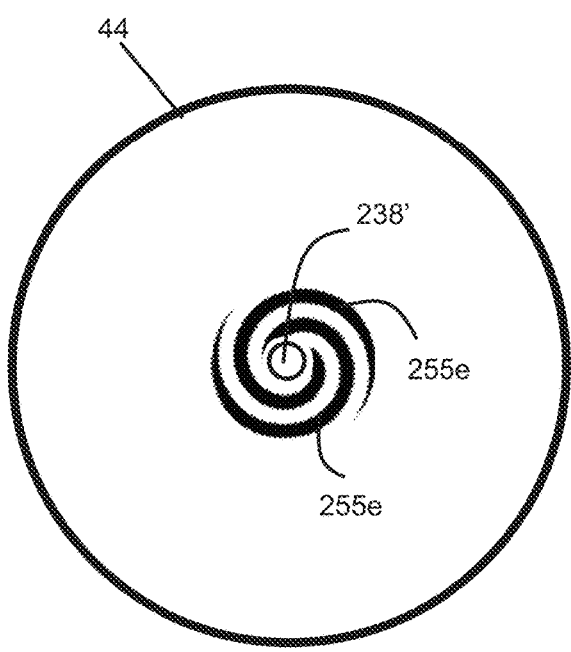
FIG. 12F is an end elevation view of a portion of the apparatus of FIG. 12A, similar to the apparatus of FIG. 12D.

FIG. 12D shows an end view of the apparatus of FIG. 12A. In one embodiment, motor 250 includes a rotating blade 255d that is a single spiral extending over the supported end 238 of rotor 230. FIG. 12F shows an alternate embodiment, in which the rotor 230 includes a plurality of nested spiral blades 255e.

Figure 13:
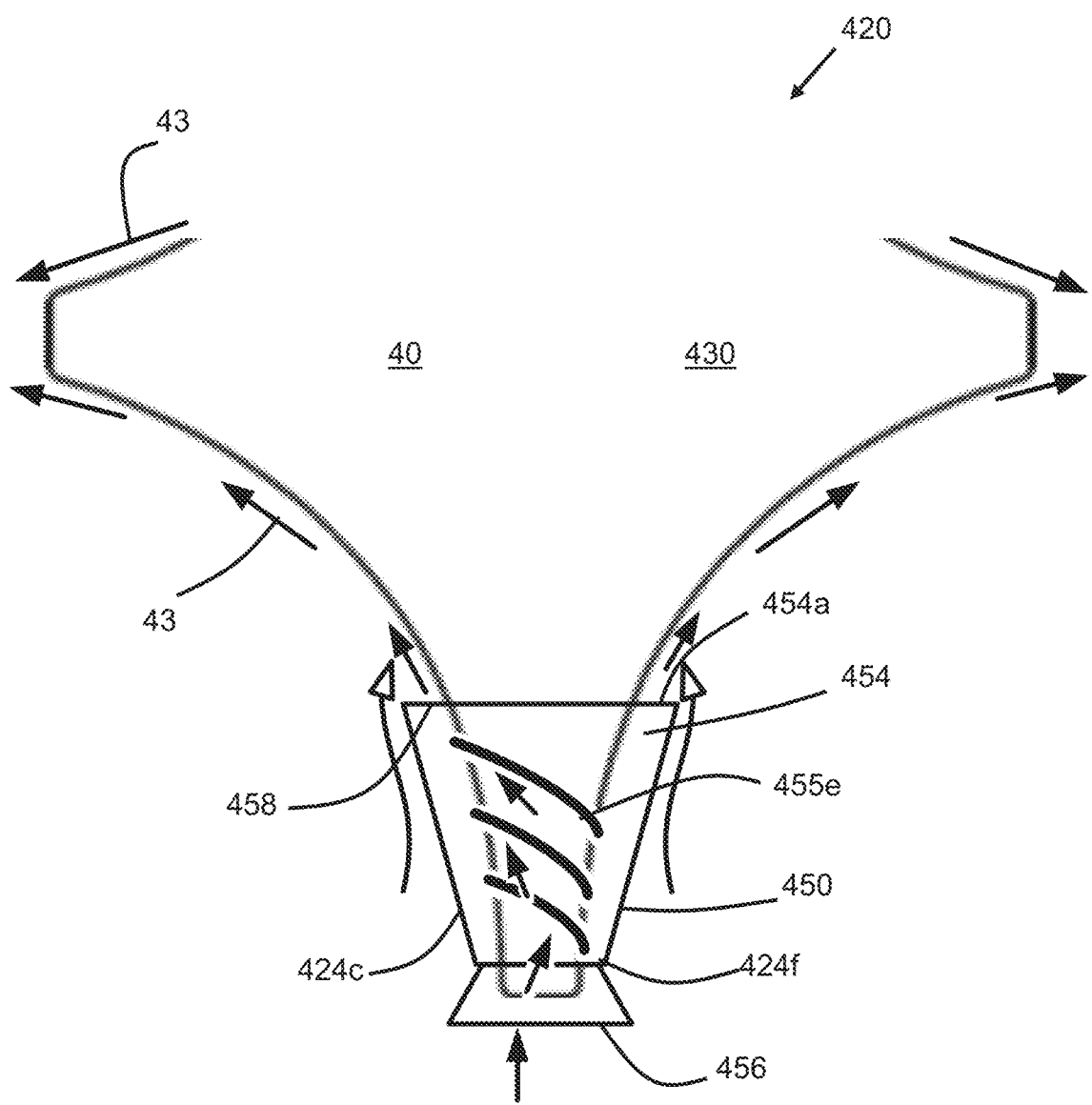
FIG. 13 is a side elevational portion of a schematic representation of a motor-driven pumping element according to another embodiment of the present invention.

FIG. 13 shows a device 420 having a rotor 430 similar to rotor 230, except including only a single motor 450 on one supported end 438. In some embodiments, the impeller 40 of body 430 is symmetric about a central plane, although in yet other embodiments impeller 430 may lack symmetry, and have different impelling outer surfaces 42 on opposing sides of apex 44.

Figure 14:
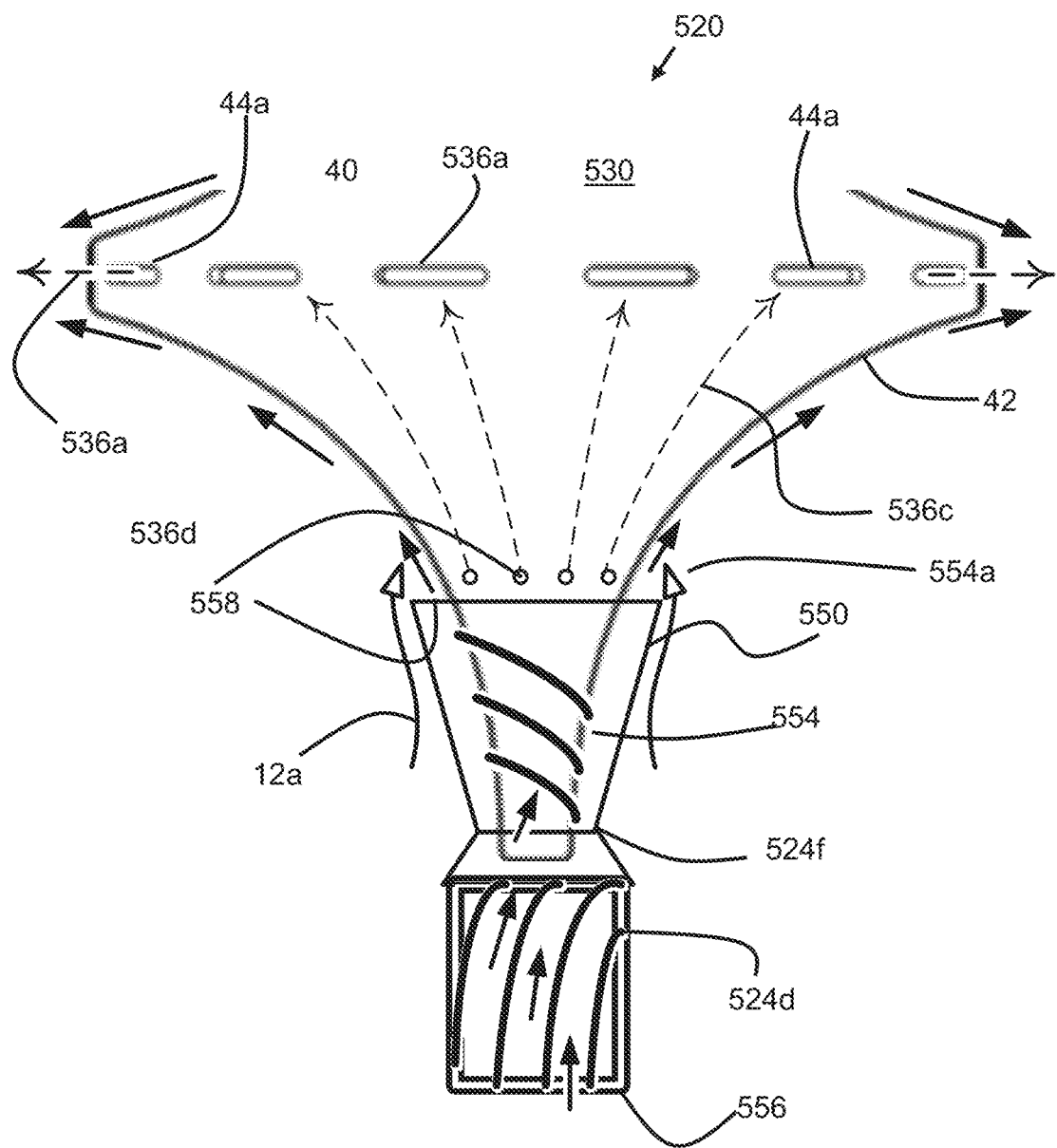
FIG. 14 is a side elevational portion of a schematic representation of a portion of a motor-driven pumping element according to another embodiment of the present invention.

FIG. 14 shows a modification of the embodiment of FIG. 13. Implanted pumping device 520 includes a motor 550 similar to motors 450 and 350. However, device 520 includes a support 524 that includes a plurality of stationary vanes 524d that impart swirl to blood received at motor entrance 556. The swirling blood flows through a converging section to a throat of minimum area 524f. In such embodiments, the combination of swirl imparted to the incoming blood, in conjunction with the higher velocity imparted to the blood by the converging nozzle, result in a motor 550 providing higher motive power and/or higher conversion efficiency.

Device 520 also includes a plurality of features adapted and configured to improve the operation of the impeller 40 of device 520. Body 530 includes a plurality of inlet holes 536d that are in rotor-internal fluid communication with a plurality of outlet apertures 44a. As has been described herein, as well as in the documents referenced herein, the apertures 44a, by virtue of being placed at apex 44 are exposed to a lower static pressure. Therefore, blood flows into orifices 536d and out of apertures 44a. This flow system is adapted and configured to reduce turbulence in mixing region 554a, by removing blood from this region. In such embodiments, the removal of flow from mixing region 554a results in an improved, re-established boundary layer on surface 42, with the result being improved overall operation of impeller 40.

Figure 15:
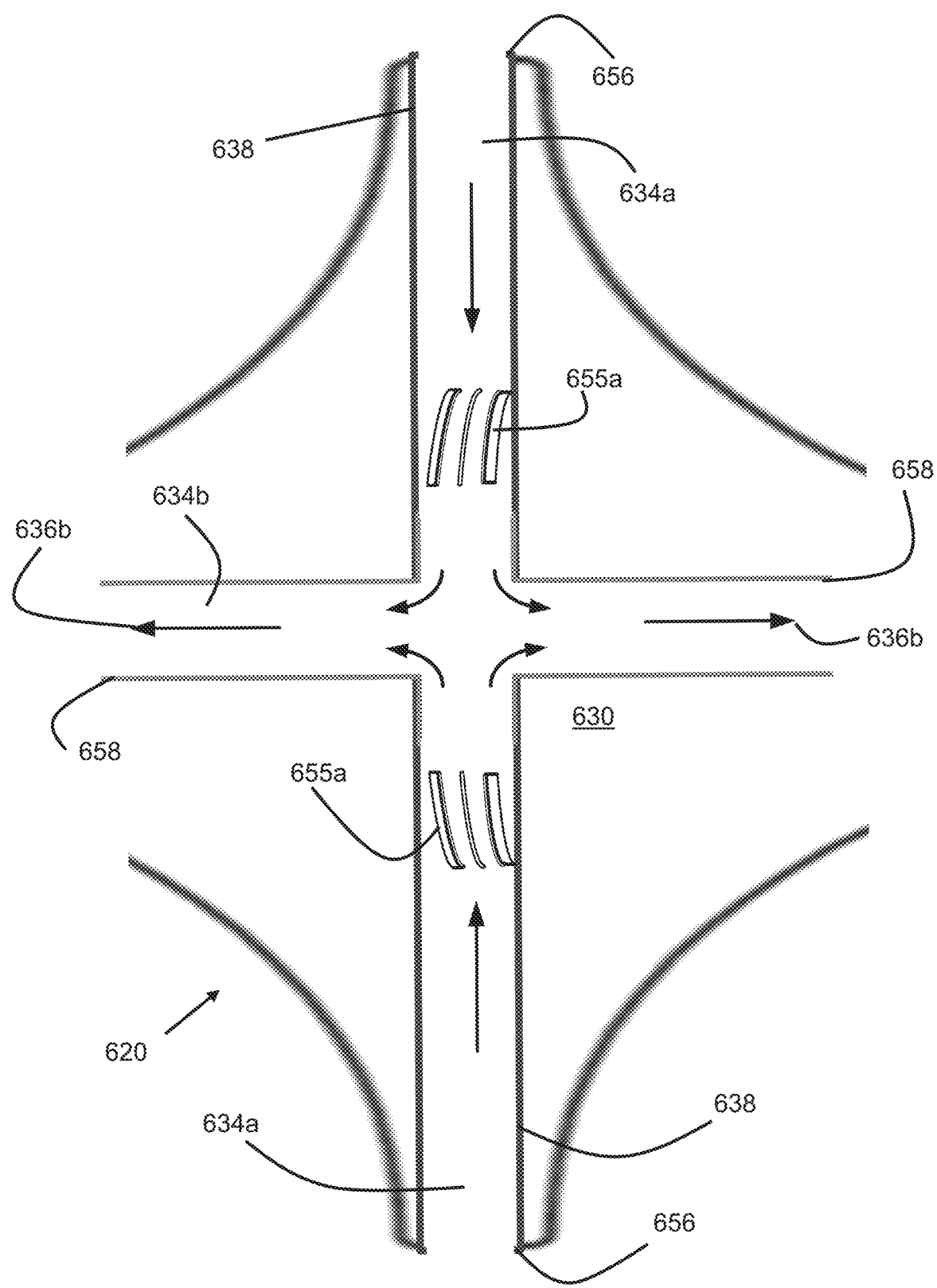
FIG. 15 is a side elevational portion of a schematic representation of a portion of a motor-driven pumping element according to another embodiment of the present invention.

FIG. 15 shows yet another example of an implantable pumping device 620 having a motor 650 with an opened flowpath 654. For the sake of clarity, FIG. 15 shows only the internal flow passages 634 of a body 630. It can be seen that body 630 includes two, opposing motor inlets 656 at each end 638 of the body. Flow from the two supply shunts 27 flow inward toward the center of body 630. In so doing, each flow encounters a plurality of motive conversion features 655a, of which only the bottom three long blades are shown, and which have at least a partial spiral shape on the inner surface of the internal flow passage. These blades function similar to the motive conversion features disclosed herein, in which energy from the flowing blood is converted into rotational energy of body 230. As the blood exits the conversion features 655, it passes into a largely unobstructed internal passageway 634c, and from there radially outward toward passageway exits 634b that are in fluid communication with apertures 44a (not shown). Therefore, the portion of blood utilized to provide motive flow exits into the Fontan receiver passages 12b.

Figure 16:
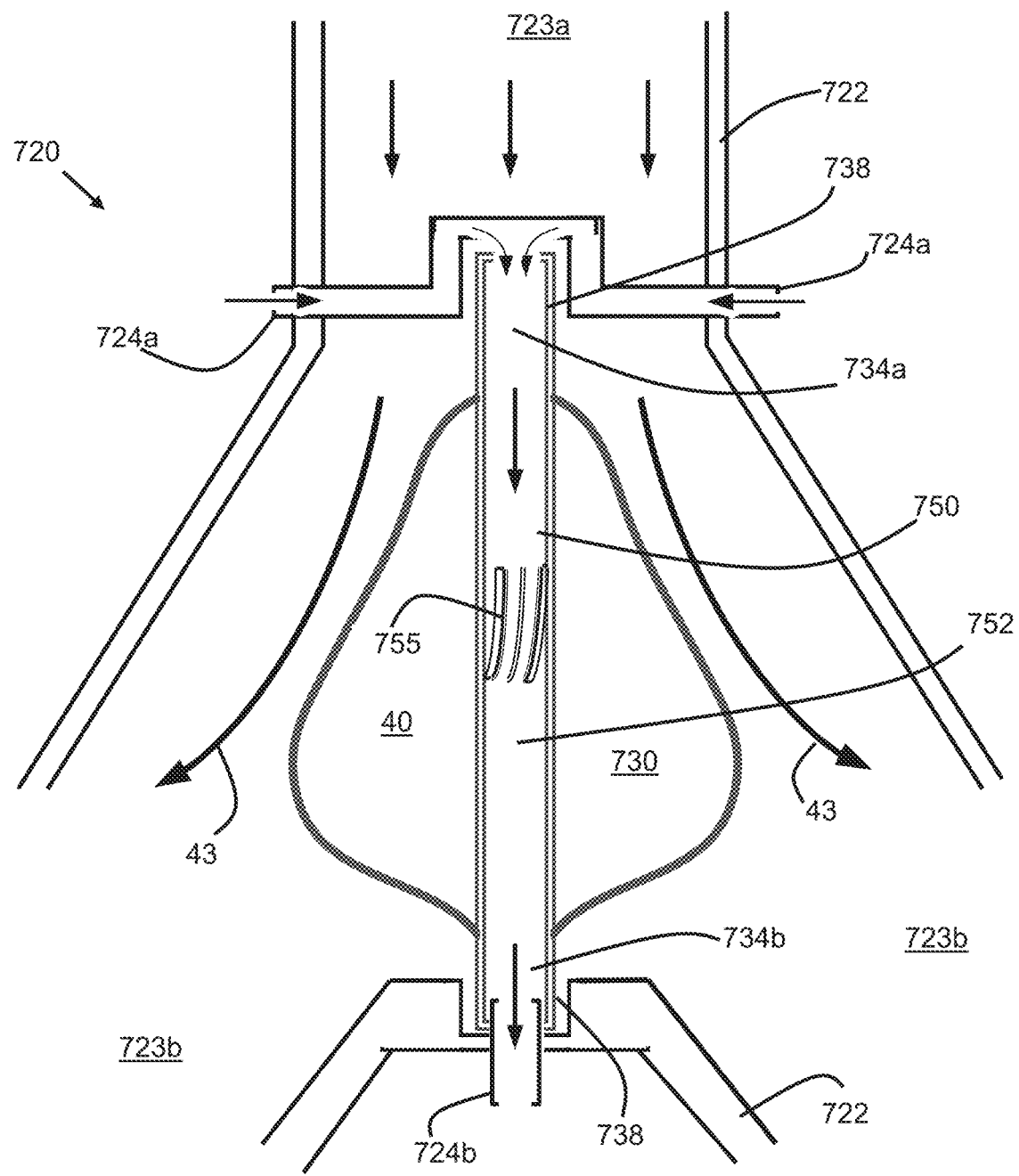
FIG. 16 is a side elevational cutaway schematic representation of a portion of a motor-driven pumping element according to another embodiment of the present invention, and useful in a branching artery.
Figure 17:
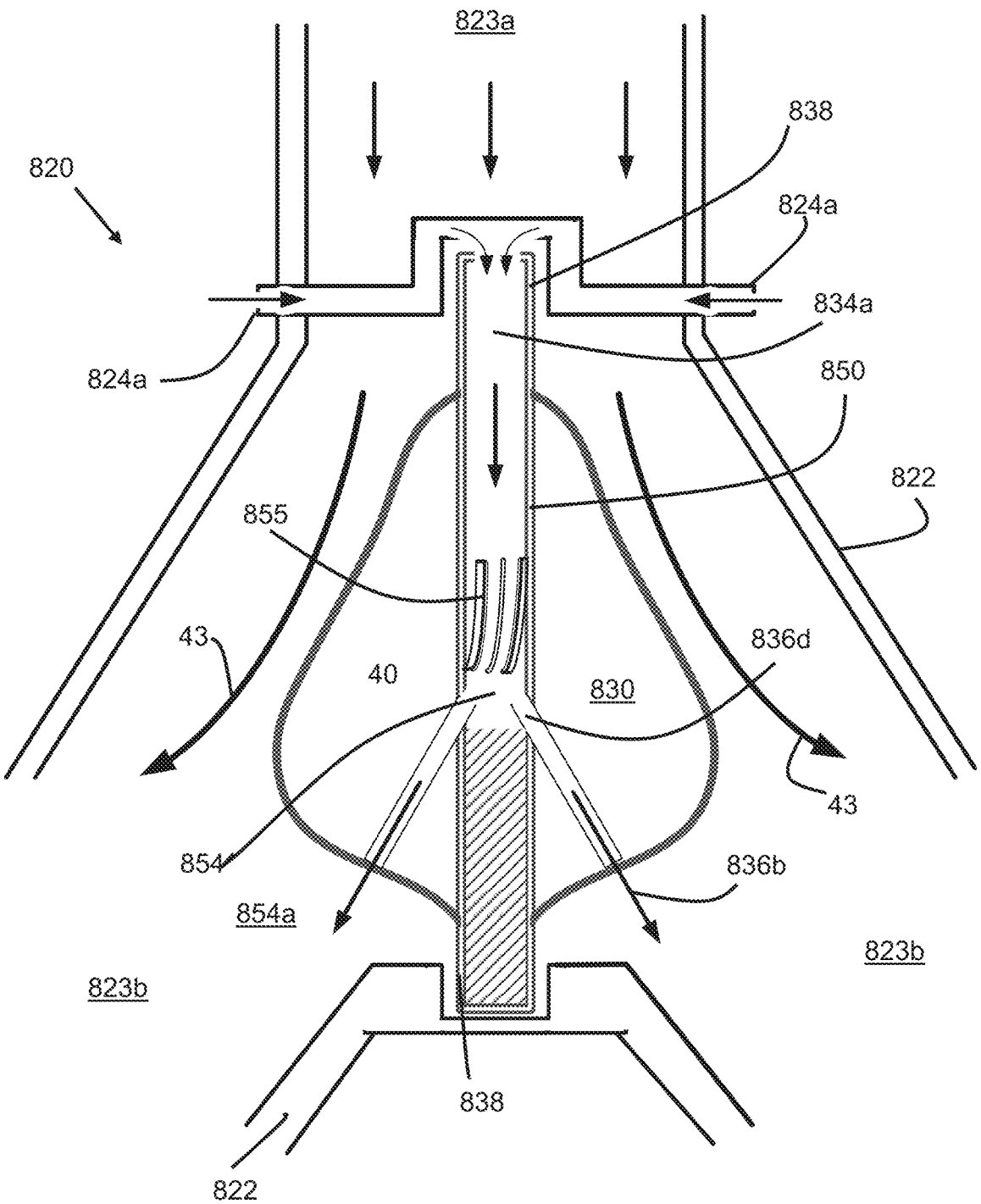
FIG. 17 is a side elevational cutaway schematic representation of a portion of a motor-driven pumping element according to another embodiment of the present invention, and useful in a branching artery.

FIGS. 16 and 17 depict devices 720 and 820, respectively, which are adapted and configured for circulatory geometries in which there is a single inlet that provides flow to a pair of outlets. FIG. 16 depicts such device with a closed flowpath hydraulic motor 752. FIG. 17 depicts a similar device with an open motor flowpath 854.

Referring to FIG. 16, it can be seen that device 720 includes a body 730 that is axisymmetric about a central rotational axis, but that is not symmetric about a plane perpendicular to that axis. The outer surface 42 of impeller 40 has a pear-shaped appearance, with a small end proximate to blood flowpath inlet 723a of housing 722. The larger diametral end of the outer surface 42 is proximate to the dual blood flowpath outlet 723. The outer surface 42 is adapted and configured to provide a centrifugal assist to blood received from inlet 723a, and increase the energy of that blood as it flows toward the exits 723b. The downstream, bulbous shape of the outer surface 42 is adapted and configured to provide low turbulence, and to not reduce the pumping efficiency of impeller 40.

FIG. 16 shows blood from one or more supply shunts 27 being provided to one or more inlets 724a of support assembly 724. Support assembly 724 further includes bearings, internal overlapping extensions, and other devices as disclosed herein. Blood from the support inlet 724a flows into the inlet 734a of the internal passage 734 of rotor 730. This blood flows over one or more motive conversion features 755 placed within the internal passageway, and which preferably extend circumferentially around the internal periphery of the passageway. After the flow imparts rotational energy to rotor 730, it exits from a support outlet 724b, and into a return shunt 28 (not shown).

FIG. 17 schematically depicts a device 820 that incorporates an opened flowpath hydraulic motor 854. As blood from inlets 824a flows into the inlets 834a of the internal passageway, the blood flows over a plurality of motive conversion features 855 that convert some of the hydraulic energy into rotational energy of rotor 830. As blood exits motor 850, it is received within one or more internal passageways 836d. These passageways extend within the body 830, and exit as shown in the downstream region of impeller 40. Preferably, the flow within passageways 836d exit into a mixing region 854a, and then into the flowpath outlet 723b. By providing the pump flow into the region of the rotor 830 that is downstream of the maximum diameter, the flow used for driving motor 850 is able to better manage the wake region, and reduce separation and turbulence in mixing region 854a, and therefore improve the pumping characteristics of rotor 40.

Various aspects of different embodiments of the present invention are expressed in paragraphs X1, X2, X3, X4, X5, X6, and X7 as follows:

X1. One aspect of the present invention pertains to a method for pumping fluid in a fluid system. The method preferably includes providing a first flow of fluid at a first higher pressure to the inlet of a hydraulic motor. The method preferably includes generating power by the motor from the first flow of fluid, and providing a second flow of fluid at a second lower pressure to the inlet of a centrifugal pump. The method preferably includes rotating the centrifugal pump with the generated power and increasing the energy of the second flow of fluid by rotating.

X2. Another aspect of the present invention pertains to a device for pumping fluid implantable in a fluid system. The device preferably includes means for pumping fluid. The device preferably includes means for hydraulically powering the pumping means, the powering means using fluid to generate the power.

X3. Yet another aspect of the present invention pertains to a device for pumping fluid implantable in a fluid system. The device preferably includes a centrifugal pump adapted and configured for increasing the kinetic energy of a first supply of fluid. The device preferably includes a hydraulic motor adapted and configured for generating power from a second supply of fluid, the motor having an inlet for receiving the second fluid supply at a higher pressure and an outlet for expelling the second fluid supply at a lower pressure; wherein flow from the outlet of the motor mixes with the first supply of fluid.

X4. Still another aspect of the present invention pertains to a device for pumping fluid implantable in a fluid system. The device preferably includes a centrifugal pump adapted and configured for increasing the kinetic energy of a first supply of fluid. The device preferably includes a hydraulic motor adapted and configured for generating power from a second supply of fluid, the motor having an inlet for receiving the second fluid supply at a higher pressure and an outlet for expelling the second fluid supply at a lower pressure; wherein flow from the outlet of the motor is discouraged from fluid communication with the first supply of fluid.

X5. Another aspect of the present invention pertains to a device for pumping fluid. The device preferably includes a hydraulic motor adapted and configured for generating power from a portion of a first supply of fluid, the motor having an inlet for receiving the portion of the first fluid supply at a first higher pressure and an outlet for expelling the first fluid supply at a first lower pressure. The device preferably includes a centrifugal pump adapted and configured for increasing the kinetic energy of the remainder of the first supply of fluid after the remainder has optionally flowed through a first restriction and exited the first restriction at a second reduced pressure, the pump being powered by the hydraulic motor, wherein the fluid at the second reduced pressure is received at an inlet of the pump, and the remainder supply of fluid is expelled from an outlet of the pump at a second increased pressure that is greater than the second reduced pressure; wherein the remainder flow at the second increased pressure optionally flows through a second restriction, and the remainder flow exiting the second restriction is in fluid communication with the portion of the first supply at the first lower pressure.

X6. Another aspect of the present invention pertains to a device for pumping fluid. The device preferably includes a centrifugal pump and a hydraulic pump. The hydraulic pump utilizes fluid to provide motive power to the pump.

X7. Yet another aspect of the present invention pertains to a device for pumping fluid. The device preferably includes a hydraulic motor adapted and configured for generating power from a portion of a first supply of fluid, the motor having an inlet for receiving the portion of the first fluid supply at a first higher pressure and an outlet for expelling the first fluid supply at a first lower pressure. The device preferably includes a centrifugal pump adapted and configured for increasing the kinetic energy of the remainder of the first supply of fluid, the pump being powered by the hydraulic motor, wherein the remainder of the first supply of fluid at a second reduced pressure less than the first higher pressure is received at an inlet of the pump, and the remainder supply of fluid is expelled from an outlet of the pump at a second increased pressure that is greater than the second reduced pressure Yet other embodiments pertain to any of the previous statements X1, X2, X3, X4, X5, X6, or X7 which are combined with one or more of the following other aspects. It is also understood that any of the aforementioned X paragraphs include listings of individual features that can be combined with individual features of other X paragraphs.

Wherein the pump includes a thin walled shell.

Wherein the pump includes opposite ends along the axis and a middle therebetween, and the outer diameter of the pump increases monotonically from each end toward the middle.

Which further comprises a housing that supports the stator, the housing including two inlets and an outlet, and in some embodiments the housing being adapted and configured to be attached to the circulatory system of the animal proximate each of the inlets.

Wherein the outlet is a first outlet and which further comprises a second outlet, the first and second outlets being located to receive fluid flowing within the plane.

Wherein the pump extends between opposing ends along a length, of the axis and which further comprises a pair of magnetic bearings, one bearing being located at one end and the other bearing being located at the other end.

Wherein each of the magnetic bearings includes a Halbach array.

Wherein each inlet of the housing includes a strut that locates the stator generally on the axis.

Wherein the external shape of the pump is adapted and configured for centrifugal pumping of fluid.

Which further comprises a plurality of apertures in the pump, the apertures being adapted and configured to permit the flow of fluid out of the flow passage.

Wherein the fluid pumped by the external shape of the pump is first received by the pump at the same position along the axis as the fluid first received and then pumped from the flow passage.

Wherein the pump includes a plurality of flow apertures providing fluid communication between the first fluid supply and the second fluid supply.

Wherein the apertures are located proximate to the plane of symmetry.

Wherein flow passage has an entry that is annular in shape.

Wherein the direction of fluid flowing within the flow passage is toward the plane of symmetry.

Wherein the direction of fluid flowing over the outer surface is toward the plane of symmetry.

Wherein said pumping means has an axis of rotation, and an inlet in which flow of blood is substantially parallel to the axis and an outlet in which flow of the pumped blood is substantially perpendicular to the axis.

Wherein said pumping means is has an outer shape as a body of revolution.

Wherein said pumping means rotates about an axis and has a body that includes an internal flowpath, and said hydraulically powering means is placed in the internal flowpath of the body.

Wherein the internal flowpath extends along the axis of rotation of said pumping means.

Wherein the internal flowpath has an inner surface surrounding the internal flowpath and said hydraulically powering means includes at least one motive conversion feature located on the inner surface Wherein the motive conversion feature is a blade.

Wherein said blade has a spiral elongated shape within the internal flowpath and along the axis of said body.

Wherein the motive conversion feature comprises a plurality of blades.

Wherein said plurality of blades each have a radial length that is less than the radius of the internal flowpath.

Wherein the motive conversion feature is a bucket having a concave side directed at least partially toward the inlet of the internal flowpath.

Wherein said pumping means has an inlet and an outlet and a body with an external centrifugal pumping surface, and said hydraulically powering means includes at least one motive conversion feature on the external surface proximate to the inlet.

Wherein the motive conversion feature is a blade.

Wherein the motive conversion feature has a spiral shape that is concentric with the axis of rotation of said pumping means.

Which further comprises a shroud proximate to the inlet that directs a portion of the blood to flow within the shroud and over said hydraulic powering means, and directs the remainder of the blood to flow over said centrifugal pumping means.

Wherein said shroud includes at least one vane for imparting swirl into the portion of the flow of blood Wherein said centrifugal pump is supported by a pair of struts and rotatable about an axis, and one said strut provides the portion of the first blood supply at the first higher pressure, and the other said strut receives the portion at the first lower pressure.

Wherein said centrifugal pump includes a rotating body with an outer surface adapted and configured to increase the kinetic energy of the remainder of the first supply of blood and an interior, the interior of the body receiving therein said hydraulic motor.

Wherein said hydraulic motor rotates along an axis and includes a rotating enclosed flowpath having a cross sectional area and a plurality of motive conversion features within the flowpath for converting some of the energy of the portion of the first blood supply to kinetic energy for powering said pump, said motive conversion features being adapted and configured to project a total surface area along the flowpath that is less than the cross sectional area of the flowpath.

Wherein the first restriction is the systemic circulatory system of a biological unit and the second restriction is the pulmonary circulatory system of the biological unit.

Wherein the remainder flow exiting the pulmonary circulatory system and the portion of the first supply at the first lower pressure from the outlet of said hydraulic motor are in fluid communication with an inlet to an atrium of the heart of the biological unit.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A device for pumping blood, comprising:
   means for centrifugally pumping blood; and
   means for hydraulically powering said pumping means, and said powering means uses blood to generate the power;
   wherein said pumping means rotates about an axis and has a body that includes an internal flowpath, and said hydraulically powering means is placed in the internal flowpath of the body; and
   wherein the internal flowpath has an inner surface surrounding the internal flowpath and said hydraulically powering means includes at least one motive conversion feature located on the inner surface.

2. The device of claim 1 wherein said pumping means has an axis of rotation, and an inlet in which flow of blood is substantially parallel to the axis and an outlet in which flow of the pumped blood is substantially perpendicular to the axis.

3. The device of claim 1 wherein said pumping means has an outer shape as a body of revolution.

4. The device of claim 1 wherein the internal flowpath extends along the axis of rotation of said pumping means.

5. The device of claim 1 wherein the motive conversion feature is a blade.

6. The device of claim 5 wherein said blade has a spiral elongated shape within the internal flowpath and along the axis of said body.

7. The device of claim 1 wherein the motive conversion feature comprises a plurality of blades.

8. The device of claim 7 wherein said plurality of blades each have a radial length that is less than the radius of the internal flowpath.

9. The device of claim 1 wherein the motive conversion feature is a bucket having a concave side directed at least partially toward the inlet of the internal flowpath.

10. The device of claim 1 wherein said pumping means has an inlet and an outlet and a body with an external centrifugal pumping surface, and said hydraulically powering means includes at least one motive conversion feature on the external surface proximate to the inlet.

11. The device of claim 10 wherein the external surface motive conversion feature is a blade.

12. The device of claim 10 wherein the external surface motive conversion feature has a spiral shape that is concentric with the axis of rotation of said pumping means.

13. The device of claim 10 which further comprises a shroud proximate to the inlet that directs a portion of the blood to flow within the shroud and over said hydraulic powering means, and directs the remainder of the blood to flow over said centrifugal pumping means.

14. The device of claim 13 wherein said shroud includes at least one vane for imparting swirl into the portion of the flow of blood.

15. A device for pumping blood, comprising:
   a hydraulic motor adapted and configured for generating power from a portion of a first supply of blood, said motor having an inlet for receiving the portion of the first blood supply at a first higher pressure and an outlet for expelling the first blood supply at a first lower pressure; and
   a centrifugal pump adapted and configured for increasing the kinetic energy of the remainder of the first supply of blood, said pump being powered by said hydraulic motor, wherein the remainder of the first supply of blood at a second reduced pressure less than the first higher pressure is received at an inlet of said pump, and the remainder supply of blood is expelled from an outlet of said pump at a second increased pressure that is greater than the second reduced pressure;
   wherein the portion of the first supply of blood expelled from the motor outlet and the remainder of the first supply of blood expelled from the pump outlet are combined and are recycled to the inlet of said motor and the inlet of said pump;
wherein said centrifugal pump is supported by a pair of struts and rotatable about an axis, and one said strut provides the portion of the first blood supply at the first higher pressure, and the other said strut receives the portion at the first lower pressure.

16. The device of claim 15 wherein said centrifugal pump includes a rotating body with an outer surface adapted and configured to increase the kinetic energy of the remainder of the first supply of blood and an interior, the interior of the body receiving therein said hydraulic motor.

17. The device of claim 15 wherein said hydraulic motor rotates along an axis and includes a rotating enclosed flowpath having a cross sectional area and a plurality of motive conversion features within the flowpath for converting some of the energy of the portion of the first blood supply to kinetic energy for powering said pump, said motive conversion features being adapted and configured to project a total surface area along the flowpath that is less than the cross sectional area of the flowpath.

18. The device of claim 15 wherein the remainder of the first supply of blood flows through a first restriction and exits the first restriction at the second reduced pressure.

19. The device of claim 18 wherein the remainder flow at the second increased pressure flows through a second restriction, and the remainder flow exiting the second restriction is in fluid communication with the portion of the first supply at the first lower pressure.

20. The device of claim 18 wherein the remainder flow at the second increased pressure flows through a second restriction, and the remainder flow exiting the second restriction is in fluid communication with the portion of the first supply at the first lower pressure.

21. The device of claim 15 which further comprises a source of blood having an inlet and an outlet, wherein said motor is adapted and configured to receive blood at the first higher pressure from the outlet of the source and provide blood at the first reduced pressure directly to the inlet.

22. The device of claim 15 wherein said pump is adapted and configured to provide the remainder supply of blood at the second increased pressure to a second restriction, the blood exits the second restriction at a third reduced pressure less than the second increased pressure, and wherein blood at the third reduced pressure is in fluid communication with blood at the first lower pressure.

23. The device of claim 15 which further comprises a source of blood having an inlet, wherein blood at the first higher pressure is provided to a first restriction and the blood exiting the first restriction is at the second reduced pressure, and said pump is adapted and configured such that blood at the second increased pressure is provided to a second restriction, and blood from the second restriction is provided to the inlet of said source.

24. The device of claim 23 wherein the first restriction is the systemic circulatory system of a biological unit and the second restriction is the pulmonary circulatory system of the biological unit.

25. The device of claim 24 wherein the remainder flow exiting the pulmonary circulatory system and the portion of the first supply at the first lower pressure from the outlet of said hydraulic motor are in fluid communication with an inlet to an atrium of the heart of the biological unit.

26. A device for pumping blood, comprising:
a hydraulic motor adapted and configured for generating power from a first supply of blood, said motor having a motor inlet for receiving the first blood supply at a first higher pressure and a motor outlet for expelling the first blood supply at a first lower pressure;
a rotatable centrifugal pump powered by said hydraulic motor and having a pump inlet and a pump outlet and an outer surface adapted and configured for increasing the kinetic energy of a second supply of blood by rotation of the outer surface, the pump inlet receiving the second supply at a second lower pressure and the second supply flowing from the pump outlet at a second higher pressure; and
wherein flow from the motor outlet at the first lower pressure is in fluid communication with the second supply of blood at the pump outlet at the second higher pressure, and the second lower pressure of the second supply of blood at the pump inlet is less than the first higher pressure of the first supply of blood at the motor inlet;
wherein said pump rotates about an axis and includes a viscously impelling outer surface shaped as a body of revolution about the axis, the body of revolution having a maximum diameter proximate to the pump outlet;
wherein said pump includes an internal passage receiving the first supply from the motor inlet, and said hydraulic motor includes a plurality of motive driving features located within the internal passage.

27. The device of claim 26 wherein the second higher pressure is a second higher total pressure, the outer surface includes at least one aperture receiving flow from the internal passage, the aperture being located proximate to the maximum diameter, the aperture and the location being adapted and configured to expose the first lower pressure to the static pressure component of the second higher total pressure.

28. A device for pumping blood, comprising:
means for centrifugally pumping blood; and
means for hydraulically powering said pumping means, and said powering means uses blood to generate the power;
wherein said pumping means has an inlet and an outlet and a body with an external centrifugal pumping surface, and said hydraulically powering means includes at least one motive conversion feature on the external surface proximate to the inlet; and
which further comprises a shroud proximate to the inlet that directs a portion of the blood to flow within the shroud and over said hydraulic powering means, and directs the remainder of the blood to flow over said centrifugal pumping means.

29. The device of claim 28 wherein said pumping means has an axis of rotation, and an inlet in which flow of blood is substantially parallel to the axis and an outlet in which flow of the pumped blood is substantially perpendicular to the axis.

30. The device of claim 28 wherein said pumping means has an axis of rotation has an outer shape as a body of revolution about the axis.

31. The device of claim 28 wherein the motive conversion feature is a blade.

32. The device of claim 31 wherein said blade has a spiral elongated shape along the axis of said body.

33. The device of claim 28 wherein the motive conversion feature comprises a plurality of blades.

34. The device of claim 28 wherein the motive conversion feature is a bucket having a concave side.

35. The device of claim 28 wherein the motive conversion feature has a spiral shape that is concentric with the axis of rotation of said pumping means.

36. The device of claim 28 which further comprises a shroud proximate to the inlet that directs a portion of the blood to flow within the shroud and over said hydraulic powering means.

37. The device of claim 36 wherein said shroud includes at least one vane for imparting swirl into the portion of the flow of blood.

38. A device for pumping blood, comprising:
a hydraulic motor adapted and configured for generating power from a portion of a first supply of blood, said motor having an inlet for receiving the portion of the first blood supply at a first higher pressure and an outlet for expelling the first blood supply at a first lower pressure; and
a centrifugal pump adapted and configured for increasing the kinetic energy of the remainder of the first supply of blood, said pump being powered by said hydraulic motor, wherein the remainder of the first supply of blood at a second reduced pressure less than the first higher pressure is received at an inlet of said pump, and the remainder supply of blood is expelled from an outlet of said pump at a second increased pressure that is greater than the second reduced pressure;
wherein the portion of the first supply of blood expelled from the motor outlet and the remainder of the first supply of blood expelled from the pump outlet are combined and are recycled to the inlet of said motor and the inlet of said pump;
wherein said centrifugal pump includes a rotating body with an outer surface adapted and configured to increase the kinetic energy of the remainder of the first supply of blood and an interior, the interior of the body receiving therein said hydraulic motor.

39. The device of claim 38 wherein said pump is adapted and configured to provide the remainder supply of blood at the second increased pressure to a second restriction and said motor is adapted and configured to provide blood at the first lower pressure to said second restriction and wherein blood at the second increased pressure is in fluid communication with blood at the first lower pressure.

40. The device of claim 38 wherein the combined first supply of blood and the remainder of the first supply of blood and provided to a second restriction before being recycled to the inlet of said motor and the inlet of said pump.

41. The device of claim 38 which further comprises a pair of struts supporting said device and rotatable about an axis, and one said strut provides the portion of the first blood supply at the first higher pressure, and the other said strut receives the portion at the first lower pressure.

42. The device of claim 38 wherein said hydraulic motor rotates along an axis and includes a rotating enclosed flowpath having a cross sectional area and a plurality of motive conversion features within the flowpath for converting some of the energy of the portion of the first blood supply to kinetic energy for powering said pump.

43. The device of claim 42 wherein, said motive conversion features being adapted and configured to project a total surface area along the flowpath that is less than the cross sectional area of the flowpath.

44. The device of claim 38 which further comprises a source of blood having an inlet, wherein blood at the first higher pressure is provided to a first restriction and the blood exiting the first restriction is at the second reduced pressure, and said pump is adapted and configured such that blood at the second increased pressure is provided to a second restriction, and blood from the second restriction is provided to the inlet of said source.

45. The device of claim 44 wherein the first restriction is the systemic circulatory system of a biological unit and the second restriction is the pulmonary circulatory system of the biological unit.

46. The device of claim 45 wherein the remainder flow exiting the pulmonary circulatory system and the portion of the first supply at the first lower pressure from the outlet of said hydraulic motor are in fluid communication with an inlet to an atrium of the heart of the biological unit.

47. The device of claim 38 wherein the remainder of the first supply of blood flows through a first restriction and exits the first restriction at the second reduced pressure.

48. The device of claim 47 wherein the remainder flow at the second increased pressure flows through a second restriction, and the remainder flow exiting the second restriction is in fluid communication with the portion of the first supply at the first lower pressure.

49. The device of claim 47 wherein the remainder flow at the second increased pressure flows through a second restriction, and the remainder flow exiting the second restriction is in fluid communication with the portion of the first supply at the first lower pressure.

* * * * *